US006242470B1

(12) United States Patent
Baxter et al.

(10) Patent No.: US 6,242,470 B1
(45) Date of Patent: Jun. 5, 2001

(54) ADAMANTANE DERIVATIVES

(75) Inventors: Andrew Baxter, Wymeswold; Stephen Brough, Selston; Thomas McInally, Loughborough; Michael Mortimore, West Bridgford, all of (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/230,511

(22) PCT Filed: Dec. 1, 1998

(86) PCT No.: PCT/SE98/02189

§ 371 Date: Jan. 26, 1999

§ 102(e) Date: Jan. 26, 1999

(87) PCT Pub. No.: WO99/29660

PCT Pub. Date: Jun. 17, 1999

(30) Foreign Application Priority Data

Dec. 5, 1997 (SE) .................................................. 9704545

(51) Int. Cl.[7] ....................... A61K 31/425; A61K 31/16; C07D 277/04; C07C 233/00
(52) U.S. Cl. ........................ 514/368; 514/369; 514/613; 514/623; 548/187; 548/205; 564/123; 564/191
(58) Field of Search ..................................... 548/187, 205; 514/368, 369, 613, 623; 564/123, 191

(56) References Cited

U.S. PATENT DOCUMENTS 3,464,998   9/1969   Krimmel .
3,789,072   1/1974   Bernstein .

FOREIGN PATENT DOCUMENTS 0 395 093      10/1990   (EP) .
0 564 924 A2   10/1993   (EP) .
95/04720        2/1995   (WO) .
95/30647       11/1995   (WO) .

OTHER PUBLICATIONS

STN Int'l, accession No. 1977:89560, Danilenko et al, "Synthesis and biological activity . . . " (1976), 10(8), 51–3.
STN Int'l, accession No. 1996:34490, Kalindjian et al, "The synthesis of a radioligand with high potency . . . " Bioorg. Med. Chem. Lett., vol. 6, No. 10, pp. 1171–1174 (1996).
STN Int'l, accession No. 1997:390174, Gibson et al, "Incorproation of conformationally constrained . . . " Bioorg. Med. Chem. Lett., vol. 7, No. 10, pp. 1289–1292 (1997).
Narayanan, V.L., "Adamantyl Analogs of 2'–(3–Dimethylaminopropylthio) . . . ," Journal of Medicinal Chemistry, vol. 15, No. 11 (1972).
Chemical Abstracts, AN: 1975:592744, "Antiviral Agents", Kreutzberger et al.
Chemical Abstracts, AN: 1974:26871, "Synthesis and biological activity . . . " Danilenko et al.
Chemical Abstracts, AN: 1968:402562, "Synthesis of adamantane derivatives . . . " Sasaki et al.
Chemical Abstracts, AN: 1975:3853, "Aliphatic acid amide . . . " Kreutzberger et al.
Syamala et al, "Modification of Photochemical Reactivity by Cyclodextrin . . . ," Tetrahedron, vol. 44, No. 23, pp. 7234 to 7242 (1988).

Primary Examiner—Deborah C. Lambkin
(74) Attorney, Agent, or Firm—Nixon & Vanderhye

(57) ABSTRACT

The invention provides adamantane derivatives, a process for their preparation, pharmaceutical compositions containing them, a process for preparing the pharmaceutical compositions, and their use in therapy.

11 Claims, No Drawings

ADAMANTANE DERIVATIVES

This application is a 371 of PCT/SE 98/02189 filed Dec. 1, 1998.

The present invention relates to adamantane derivatives, a process for their preparation, pharmaceutical compositions containing them, a process for preparing the pharmaceutical compositions, and their use in therapy.

Adamantane derivatives are known in the art, e.g. from U.S. Pat. No. 3,789,072 as serotonin inhibitors, from Chem. Abs. (1974), Vol. 80, No.5 (26871m) as inflammation and edema inhibitors or analgesics, from Chem. Abs. (1975), Vol. 82, No.1 (3853j) and Chem. Abs. (1977), Vol. 86, No.17 (120855e) as antiviral agents, and also from Chem. Abs. (1968), Vol. 69, No.1 (2562h), Chem. Abs. (1975), Vol. 82, No. 3 (16510v) and Tetrahedron (1988), 44, No. 23, 7234–7242.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and L-selectin shedding (lymphocytes). $P2X_7$ receptors are also located on antigen-presenting cells (APC), keratinocytes, salivary acinar cells (parotid cells) and hepatocyte.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of general formula

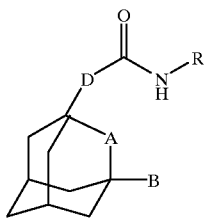

(I)

wherein A represents a group $CH_2$ or an oxygen atom; B represents a hydrogen or halogen atom (e.g. fluorine, chlorine, iodine and especially bromine);

D represents a group $CH_2$, $OCH_2$, $NHCH_2$ or $CH_2CH_2$, in particular a group $CH_2$, $OCH_2$ or $NHCH_2$;

R represents a phenyl, benzothiazolyl, indolyl, indazolyl, purinyl, pyridyl, pyrimidinyl or thiophenyl group, each of which may be optionally substituted by one or more substituents independently selected from a halogen atom or a cyano, carboxyl, hydroxyl, nitro, halo-$C_1$–$C_6$-alkyl, —N($R^1$)—C(=O)—$R^2$, —C(O)N$R^3R^4$, —N$R^5R^6$, $C_3$–$C_8$-cycloalkyl, 3- to 8-membered heterocyclyl, $C_3$–$C_8$-cycloalkyloxy, $C_1$–$C_6$-alkylcarbonyl, phenoxy, benzyl, $C_1$–$C_6$-alkylthio, phenylthio, $C_1$–$C_6$-alkoxycarbonyl, $C_1$–$C_6$-alkylsulphinyl or $C_1$–$C_6$-alkylsulphonyl group, or a $C_1$–$C_6$-alkyl or $C_1$–$C_6$-alkoxy group optionally substituted by one or more substituents independently selected from a halogen atom or an amino, carboxyl, hydroxyl, $C_1$–$C_6$-alkoxy, (di)$C_1$–$C_6$-alkylamino, $C_1$–$C_6$-alkoxycarbonyl, imidazolyl, morpholinyl, piperidinyl or pyrrolidinyl group;

$R^1$ represents a hydrogen atom or a $C_1$–$C_6$-alkyl or $C_3$–$C_8$-cycloalkyl group;

$R^2$ represents a $C_1$–$C_6$-alkyl or $C_3$–$C_8$-cycloalkyl group; and $R^3$, $R^4$, $R^5$ and $R^6$ each independently represent a hydrogen atom or a $C_1$–$C_6$-alkyl or $C_3$–$C_8$-cycloalkyl group;

with the provisos that when A is $CH_2$, B is H and D is $CH_2$, then R does not represent a phenyl, ortho-carboxyphenyl, methylphenyl or para-phenoxyphenyl group, and that when A is $CH_2$, D is $CH_2$ or $CH_2CH_2$ and R represents a substituted phenyl group, the substituent or substituents present do not comprise, in an ortho position, a $C_1$–$C_6$-alkoxy group substituted by an amino, (di)$C_1$–$C_6$-alkylamino, imidazolyl, morpholinyl, piperidinyl or pyrrolidinyl group;

or a pharmaceutically acceptable salt or solvate thereof.

In the context of the present specification, unless otherwise indicated, an alkyl substituent or alkyl moiety in a substituent group may be linear or branched. Furthermore, the (cyclo)alkyl moieties in a dialkylamino, dicycloalkylamino, dialkylamido or dicycloalkylamido substituent group may be the same or different. When D represents a group $OCH_2$ or $NHCH_2$, the group is orientated such that the oxygen or nitrogen atom is directly attached to the adamantyl group. A 3- to 8-membered heterocyclyl group should be understood to mean an aliphatic heterocyclic ring system containing a single heteroatom selected from nitrogen, oxygen or sulphur. The term "in an ortho position" defines the ring position on the phenyl ring of R which is adjacent to the point of attachment of the amide linking group to R, e.g., as illustrated in the formula below where the asterisks define the "ortho position":

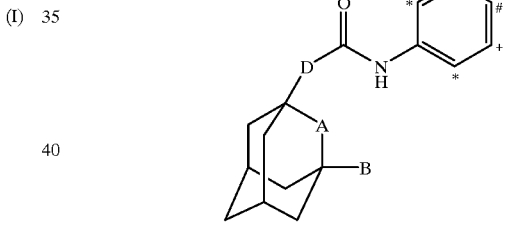

Similarly, meta and para positions in the phenyl group R are defined relative to the point of attachment of the amide linking group to R and are indicated in the above formula by the symbols + and # respectively.

Preferably, R represents a phenyl, benzothiazolyl, indolyl, indazolyl, purinyl, pyridyl, pyrimidinyl or thiophenyl group, each of which may be optionally substituted by one, two, three or four substituents independently selected from a halogen atom (e.g. fluorine, chlorine, bromine or iodine) or a cyano, carboxyl, hydroxyl, nitro, halo-$C_1$–$C_6$-alkyl (e.g. trifluoromethyl), —N($R^1$)—C(=O)—$R^2$, —C(O)N$R^3R^4$, —N$R^5R^6$, $C_3$–$C_8$-cycloalkyl (e.g. cyclopropyl, cyclobutyl, cyclopentyl or cyclohexyl), 3- to 8-membered heterocyclyl (e.g. aziridinyl, pyrrolidinyl, piperidinyl), $C_3$–$C_8$-cycloalkyloxy (e.g. cyclopropyloxy, cyclobutyloxy, cyclopentyloxy or cyclohexyloxy), $C_1$–$C_6$-alkylcarbonyl (e.g. methyl-, ethyl-, propyl-, butyl-, pentyl- or hexylcarbonyl), phenoxy, benzyl, $C_1$–$C_6$-alkylthio (e.g. methyl-, ethyl-, propyl-, butyl-, pentyl- or hexylthio), phenylthio, $C_1$–$C_6$-alkoxycarbonyl (e.g. methoxy-, ethoxy-, propoxy-, butoxy-, pentoxy- or hexoxycarbonyl), $C_1$–$C_6$-alkylsulphinyl (e.g. methyl-, ethyl-, propyl-, butyl-, pentyl- or hexylsulphinyl), or $C_1$–$C_6$-alkylsulphonyl (e.g. methyl-, ethyl-, propyl-, butyl-, pentyl- or hexylsulphonyl) group, or a $C_1$–$C_6$-alkyl (e.g. methyl, ethyl, propyl, butyl, pentyl or hexyl) or $C_1$–$C_6$-alkoxy (e.g. methoxy-, ethoxy-, propoxy-, butoxy-, pentoxy- or hexoxy) group optionally substituted by one, two, three or four substituents independently selected from a halogen atom (e.g. fluorine, chlorine, bromine or iodine) or an amino, carboxyl, hydroxyl, $C_1$–$C_6$-alkoxy (e.g. methoxy, ethoxy, propoxy, butoxy, pentoxy or hexoxy), (di)$C_1$–$C_6$-alkylamino (e.g.(di)methylamino or (di)ethylamino), $C_1$–$C_6$-alkoxycarbonyl (e.g. methoxy-, ethoxy-, propoxy-, butoxy-, tert-butoxy-, pentoxy- or hexoxycarbonyl), imidazolyl, morpholinyl, piperidinyl or pyrrolidinyl group.

More preferably, R represents a phenyl, benzothiazolyl, indolyl, indazolyl, purinyl, pyridyl or thiophenyl group, each of which may be optionally substituted by one, two or three substituents independently selected from a halogen atom (especially chlorine) or a hydroxyl, nitro or $C_1$–$C_4$-alkoxycarbonyl (in particular methoxycarbonyl) group, or a $C_1$–$C_4$-alkyl (most preferably $C_1$–$C_2$-alkyl) or $C_1$–$C_4$-alkoxy (most preferably $C_1$–$C_3$-alkoxy) group optionally substituted by one or two substituents independently selected from a halogen atom or an amino, carboxyl, hydroxyl, $C_1$–$C_4$-alkoxy (especially methoxy), (di)$C_1$–$C_4$-alkylamino (in particular methylamino or dimethylamino), $C_1$–$C_4$-alkoxycarbonyl(especially tert-butoxycarbonyl), imidazolyl, morpholinyl, piperidinyl or pyrrolidinyl group.

It is preferred that $R^1$ represents a hydrogen atom or a $C_1$–$C_4$-alkyl (e.g. methyl, ethyl, propyl or butyl) or $C_3$–$C_6$-cycloalkyl (e.g. cyclopentyl or cyclohexyl) group.

Preferably $R^2$ represents a $C_1$–$C_4$-alkyl (e.g. methyl, ethyl, propyl or butyl) or $C_3$–$C_6$-cycloalkyl (e.g. cyclopentyl or cyclohexyl) group.

Preferably, $R^3$, $R^4$, $R^5$ and $R^6$ each independently represent a hydrogen atom or a $C_1$–$C_4$-alkyl (e.g. methyl, ethyl, propyl or butyl) or $C_3$–$C_6$-cycloalkyl (e.g. cyclopentyl or cyclohexyl) group.

Preferred compounds of the invention include:

N-(2-Methyl-6-benzothiazolyl)-tricyclo[3.3.1.1$^{3,7}$]decane-1-acetamide,

N-(3-(3-(Aminopropyloxy)-2-methylphenyl)-tricyclo[3.3.1.1$^{3,7}$]decane-1-acetamide, hydrochloride, N-(2-Chlorophenyl)-tricyclo[3.3.1.1$^{3,7}$]decane-1-acetamide, N-(2,4,5-Trimethylphenyl)-tricyclo[3.3.1.1$^{3,7}$]decane-1-acetamide, N-(5-Methoxy-2-methylphenyl)-tricyclo[3.3.1.1$^{3,7}$]decane-1-acetamide, N-(2,3-Dimethylphenyl)-tricyclo[3.3.1.1$^{3,7}$]decane-1-acetamide, N-(5-Indolyl)-tricyclo[3.3.1.1$^{3,7}$]decane-1-acetamide, N-(2,3-Dimethyl-5-indolyl)-tricyclo[3.3.1.1$^{3,7}$]decane-1-acetamide, N-[5-(3-N,N-Dimethylaminopropoxy)-2-methylphenyl]-tricyclo[3.3.1.1$^{3,7}$]decane-1-acetamide, hydrochloride, N-(5-Indazolyl)-tricyclo[3.3.1.1$^{3,7}$]decane-1-acetamide, N-(6-Indazolyl)-tricyclo[3.3.1.1$^{3,7}$]decane-1-acetamide, N-(5-Hydroxy-2-methylphenyl)-tricyclo[3.3.1.1$^{3,7}$]decane-1-acetamide, N-(1H-Indol-4-yl)-tricyclo[3.3.1.1$^{3,7}$]decane-1-acetamide, 4-Methyl-3-[[1-oxo-2-(tricyclo[3.3.1.1$^{3,7}$]dec-1-yl)ethyl]amino]phenoxy-acetic acid, hydrochloride salt, N-(1-Methyl-1H-indol-5-yl)-tricyclo[3.3.1.1$^{3,7}$]decane-1-acetamide, N-(1-(N,N-Dimethylamino)ethyl-1H-indo-5-yl)-tricyclo[3.3.1.1$^{3,7}$]decane-1-acetamide, 5-[[1-Oxo-2-(tricyclo[3.3.1.1$^{3,7}$]dec-1-yl)ethyl]amino]-1H-indole-1-acetic acid, 1,1-dimethylethyl ester, N-(3-(2-Chloropyridyl))-tricyclo[3.3.1.1$^{3,7}$]decane-1-acetamide, N-(3-(N,N-Dimethylamino)methyl-1H-indo-5-yl)-tricyclo[3.3.1.1$^{3,7}$]decane-1-acetamide, N-(4-Methoxy-2-methylphenyl)-tricyclo[3.3.1.1$^{3,7}$]decane-1-acetamide, N-(2-Chloro-5-methoxyphenyl)-tricyclo[3.3.1.1$^{3,7}$]decane-1-acetamide, N-(4-Hydroxy-2-methylphenyl)-tricyclo[3.3.1.1$^{3,7}$]decane-1-acetamide, N-(3-Hydroxymethyl-2-methylphenyl)-tricyclo[3.3.1.1$^{3,7}$]decane-1-acetamide, N-(5-Methoxy-2-methyl-3-nitrophenyl)-tricyclo[3.3.1.1$^{3,7}$]decane-1-acetamide, N-(5-Hydroxymethyl-2-methylphenyl)-tricyclo[3.3.1.1$^{3,7}$]decane-1-acetamide, N-(3-Hydroxy-2-methylphenyl)-tricyclo[3.3.1.1$^{3,7}$]decane-1-acetamide, N-(2-Methyl-5-(1-pyrrolidinemethyl)phenyl)-tricyclo[3.3.1.1$^{3,7}$]decane-1-acetamide, hydrochloride, N-(2-Chloro-5-hydroxyphenyl)-tricyclo[3.3.1.1$^{3,7}$]decane-1-acetamide, N-(2-Chloro-4-hydroxyphenyl)-tricyclo[3.3 1.1$^{3,7}$]decane-1-acetamide, N-(2-Methyl-3-(2-(1-pyrrolidino)ethyloxy)phenyl)-tricyclo[3.3.1.1$^{3,7}$]decane-1-acetamide, hydrochloride, N-(5-Methoxymethyl-2-methylphenyl)-tricyclo[3.3.1.1$^{3,7}$]decane-1-acetamide, N-(2-Methyl-3-(2-(1-morpholino)ethyloxy)phenyl)-tricyclo[3.3.1.1$^{3,7}$]decane-1-acetamide, hydrochloride, N-(2-Methyl-3-(2-(1-piperidino)ethyloxy)phenyl)-tricyclo[3.3.1.1$^{3,7}$]decane-1-acetamide, hydrochloride, N-(2-Methyl-5-(1-morpholinomethyl)phenyl)-tricyclo[3.3.1.1$^{3,7}$]decane-1-acetamide, hydrochloride, N-(5-(3-(2-N,N-dimethylaminoethyl)indolyl))-tricyclo[3.3.1.1$^{3,7}$]decane-1-acetamide, hydrochloride, Methyl 4-methyl-3-[[1-oxo-2-(tricyclo[3.3.1.1$^{3,7}$]dec-1-yl)ethyl]amino]thiophene-2-carboxylate, N-(3-Methoxy-2-methylphenyl)-tricyclo[3.3.1.1$^{3,7}$]decane-1-acetamide, N-(2-Methyl-3-(2-(1-imidazolo)ethyloxy)phenyl)-tricyclo[3.3.1.1$^{3,7}$]decane-1-acetamide, N-(2,4,6-Trimethylphenyl)-tricyclo[3.3.1.1$^{3,7}$]decane-1-acetamide, N-(5-(3-Aminopropyloxy)-2-methylphenyl)-tricyclo[3.3.1.1$^{3,7}$]decane-1-acetamide, hydrochloride, N-(5-(3-(N-Methylamino)propyloxy)-2-methylphenyl)-tricyclo[3.3.1.1$^{3,7}$]decane-1-acetamide, hydrochloride, N6-(Tricyclo[3.3.1.1$^{3,7}$]decane-1-acetyl)adenine, N-(3,5-Dimethoxy-2-methylphenyl)-tricyclo[3.3.1.1$^{3,7}$]decane-1-acetamide, N-(3-(3-(N-Methylamino)propyloxy)-2-methylphenyl)-tricyclo[3.3.1.1$^{3,7}$]decane-1-acetamide, hydrochloride, N-(5-(3-(N,N-Dimethylamino)propyloxy)-2-methylphenyl)-tricyclo[3.3.1.1$^{3,7}$]decane-1-acetamide, hydrochloride, N-(5-Methoxy-2-methylphenyl)-tricyclo[3.3.1.1$^{3,7}$]decanyloxy-1-acetamide, N-(5-Methoxy-2-methylphenyl)-(3-bromo-tricyclo[3.3.1.1$^{3,7}$]decane)-1-acetamide, N-(5-Methoxy-2-methylphenyl)-(2-oxa-tricyclo[3.3.1.1$^{3,7}$]decane)-1-acetamide, N-(5-Methoxy-2-methylphenyl)-2-(tricyclo[3.3.1.1³,⁷]decan-1-amino)acetamide, N-(3,5-Dimethoxyphenyl)-tricyclo[3.3.1.1³,⁷]decane-1-acetamide, N-(3,5-Dihydroxyphenyl)-tricyclo[3.3.1.1³,⁷]decane-1-acetamide, N-(3,5-Dimethoxyphenyl)-tricyclo[3.3.1.1³,⁷]decanyloxy-1-acetamide, N-(3,5-Bis-(3-aminopropyloxy)phenyl)-tricyclo[3.3.1.1³,⁷]decane-1-acetamide, N-(2,4,5-Trimethylphenyl)-tricyclo[3.3.1.1³,⁷]decanyloxy-1-acetamide, N-(5-Hydroxy-2-methylphenyl)-tricyclo[3.3.1.1³,⁷]decanyloxy-1-acetamide, N-(5-(2-(N-Methylamino)ethyloxy)-2-methylphenyl)-tricyclo[3.3.1.1³,⁷]decane-1-acetamide, hydrochloride, N-(5-(2-(N-Methylamino)ethyloxy)-2-methylphenyl)-tricyclo[3.3.1.1³,⁷]decanyloxy-1-acetamide, N-(5-(3-(N-Methylamino)propyloxy)-2-methylphenyl)-tricyclo[3.3.1.1³,⁷]decanyloxy-1-acetamide, and N-(3,5-Dihydroxy-2-methylphenyl)-tricyclo[3.3.1.1³,⁷]decane-acetamide.

The present invention further provides a process for the preparation of a compound of formula (I) as defined above which comprises reacting a compound of general formula (II)

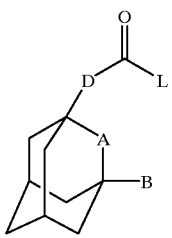

wherein L represents a leaving group (e.g. a halogen atom such as chlorine or an imidazole group) and A, B and D are as defined in formula (I), with a compound of general formula (III), R—NH₂, wherein R is as defined in formula (I); and optionally forming a pharmaceutically acceptable salt or solvate thereof.

The process may conveniently be carried out in a solvent (e.g. acetonitrile, N,N-dimethylformamide or dichloromethane) and optionally in the presence of a base (e.g. triethylamine, 4-dimethylaminopyridine ordiisopropylethylamine). The process is conveniently operated at a temperature in the range from 0 to 100° C., preferably in the range from 10 to 80° C., and especially at ambient temperature (20° C.).

The compounds of formula (II) and (III) are known compounds or may be prepared by processes analogous to those known in the art.

It will be appreciated by those skilled in the art that in the process of the present invention certain functional groups such as hydroxyl or amino groups in ithe intermediate compounds may need to be protected by protecting groups. Thus, the final stage in the preparation of the compounds of formula (I) may involve the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity. They are therefore indicated as pharmaceuticals for use in the treatment or prevention of rheumatoid arthritis, osteoarthritis, psoriasis, allergic dermatitis, asthma, hyperresponsiveness of the airway, septic shock, glomeruloneplhritis, irritable bowel disease, Crohn's disease, ulcerative colitis, atherosclerosis, growth and metastases of malignant cells, myocardial ischaemia, myoblastic leukaernia, diabetes, Alzheimer's disease, osteoporosis, burn injury, stroke, varicose veins and meningitis.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disorder indicated.

The compounds of formula (I) and pharmaceutically acceptable salts aid solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will be further understood by reference to the following illustrative examples in which the terms MS, NMR, CDCl$_3$ and DMSO denote respectively mass spectrometry, nuclear magnetic resonance, chloroform-d and dimethylsulphoxide.

EXAMPLE 1

N-(2-Methyl-6-benzothiazolyl)-tricyclo[3.3.1.1$^{3,7}$]decane-1-acetamide

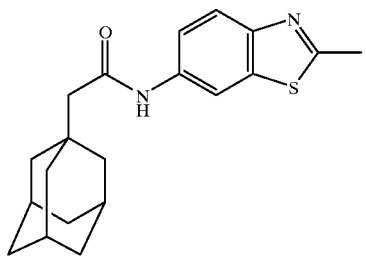

a) 1-Adamantaneacetyl Chloride

A solution of 1-adamantaneacetic acid (4.5 g) in thionyl chloride (20 ml) was heated at reflux temperature for 24 hours and then allowed to cool to ambient temperature. The excess thionyl chloride was removed under reduced pressure to leave the sub-title compound as a syrup (4.9 g).

b) N-(2-Methyl-6-benzothiazolyl)-tricyclo[3.3.1.1$^{3,7}$]decane-1-aceimde

To a solution of 1-adamantaneacetyl chloride (0.5 g) prepared as described in a) above in acetonitrile (10 ml) was added triethylamine (0.38 ml) and 6-amino-2-methylbenzothiazole (0.39 g). The reaction mixture was stirred at ambient temperature for 1 hour before being diluted with ethyl acetate. The organic phase was then washed with dilute hydrochloric acid and water, dried over magnesium sulphate (MgSO$_4$) and finally concentrated under reduced pressure to give the title compound as a white solid (0.12 g).

Melting point: 172° C.; MS (APCI+ve) 341 (M+H)$^+$; $^1$H NMR (CDCl$_3$) δ 8.45 (1H, d), 7.84 (1H, d), 7.19 (2H, m), 2.81 (3H, s), 2.13 (2H, s), 2.00 (3H, s), 1.75 (12H, m).

EXAMPLE 2

N-(3-(3-(Aminopropyloxy)-2-methylphenyl)-tricyclo[3.3.1.1$^{3,7}$]decane-1-acetamide, hydrochloride

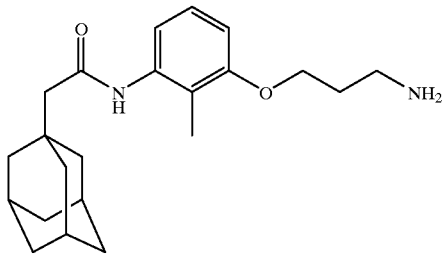

Diethyl azodicarboxylate (1.0 ml) was added to a solution of N-(3-hydroxy-2-methylphenyl)-tricyclo[3.3.1.1$^{3,7}$]decane-1-acetamide (0.408 g, Example 26), tert-butyl N-(3-hydroxypropyl)carbamate (1.11 g) and triphenylphosphine (1.74 g) in tetrahydrofuran (5 ml). After stirring overnight at room temperature the reaction mixture was concentrated under reduced pressure. The residue was purified by column chromatography over silica eluting with dichloromethane:ethyl acetate (9:1) and then further purified by HPLC over a Dynamax® column using a Waters Prep 4000 eluting with iso-hexane:ethyl acetate (7:3) to give the Mitsunobu reaction product (0.34 g) which was dissolved in methanol (10 ml). A solution of hydrogen chloride (generated by slow addition of acetyl chloride (12 ml) to methanol (10 ml) at 0° C. CARE—Very Exothermic) was then added to the latter solution and the reaction stirred at room temperature for 2 hours. The reaction was partitioned between saturated aqueous sodium hydrogen carbonate (100 ml) and extracted with ethyl acetate (100 ml). The organic extract was dried over anhydrous sodium sulphate, filtered and concentrated under reduced pressure. The residue was purified by slica gel chromatography eluting with dichloromethane:ethanol:triethylamine (18:2:1) to give a yellow oil. The latter was dissolved in methanol (10 ml) and dichloromethane (2 ml) and treated with an ethereal solution of hydrogen chloride (1M, 5 ml). After 2 minutes the solvents were removed under reduced pressure. The residual gum was stirred in ether:iso-hexane (1:1) overnight, the solvent removed by filtration to leave the title compound as a solid (0.186 g) which was isolated by decanting the solvent then drying the residue.

MS (APCI+ve) 357 (M−HCl+H)$^+$; $^1$H NMR (DMSO-d$_6$) δ 9.20 (1H, s), 7.97 (3H, bs), 7.10 (1H, t), 6.94 (1H, d), 6.77 (1H, d), 4.05 (2H, t), 3.05–2.9 (2H, m), 2.1–2.0 (7H, m), 1.94 (3H, s), 1.75–1.55 (12H, m).

EXAMPLE 3

N-(2-Chlorophenyl)-tricyclo[3.3.1.1$^{3,7}$]decane-1-acetamide

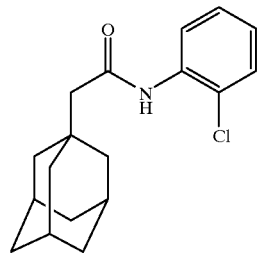

Prepared according to the method of Example 1b) from 1-adamantaneacetyl chloride (0.2 g) and 2-chlorolaniline (0.12 g) to give the title compound as a white solid (0.05 g).

Melting point: 122–124° C.; MS (APCI+ve) 304/306 (M+H)$^+$; $^1$H NMR (CDCl$_3$) δ 8.40 (1H, d), 7.55 (1H, s), 7.40 (1H, dd), 7.3 (1H, m), 7.05 (1H, m), 2.16 (2H, s), 2.00 (3H, s), 1.75 (12H, m).

EXAMPLE 4

N-(2,4,5-Trimethylphenyl)-tricyclo[3.3.1.1$^{3,7}$]decane-1-acetamide

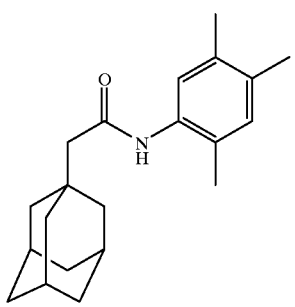

Prepared according to the method of Example 1b) from 1-adamantaneacetyl chloride (0.2 g) and 2,4,5-trimethylaniline (0.13 g) to give the title compound as a white solid (0.042 g).

Melting point: 158° C.; MS (APCI+ve) 312 (M+H)$^+$; $^1$H NMR (DMSO-d$_6$) δ 9.00 (1H, s), 7.08 (1H, s), 6.94 (1H, s), 2.14 (6H, s), 2.10 (3H, s), 2.04 (2H, s), 1.98 (3H, s), 1.75 (12H, m).

EXAMPLE 5

N-(5-Methoxy-2-methylphenyl)-tricyclo[3.3.1.1$^{3,7}$]decane-1-acetamide

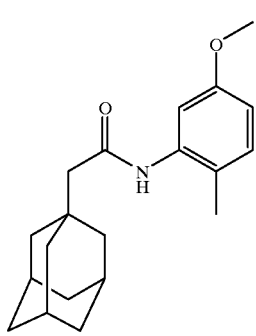

Prepared according to the method of Example 1b) from 1-adamantaneacetyl chloride (0.2 g) and 5-methoxy-2-methylaniline (0.13 g) to give the title compound as a white solid (0.043 g).

Melting point: 147° C.; MS (APCI+ve) 314 (M+H)$^+$; $^1$H NMR (DMSO-d$_6$) 9.00 (1H, s), 7.07 (1H, d), 7.04 (1H, d), 6.65 (1H, dd), 3.69 (3H, s), 2.13 (3H, s), 2.09 (2H, s), 1.95 (3H, s), 1.75 (12H, m).

EXAMPLE 6

N-(2,3-Dimethylphenyl)-tricyclo[3.3.1.1$^{3,7}$]decane-1-acetamide

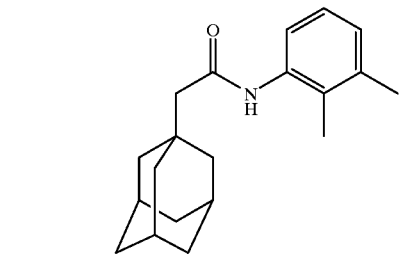

Prepared according to the method of Example 1b) from 1-adamantaneacetyl chloride (0.2 g) and 2,3-dimethylaniline (0.11 g) to give the title compound as a white solid (0.034 g).

Melting point: 170° C.; MS (APCI+ve) 298 (M+H)$^+$; $^1$H NMR (DMSO-d$_6$) δ 9.20 (1H, s), 7.20–6.95 (3H, m), 2.23 (3H, s), 2.07 (5H, s), 1.95 (3H, s), 1.75 (12H, m).

EXAMPLE 7

N-(5-Indolyl)-tricyclo[3.3.1.1$^{3,7}$]decane-1-acetamide

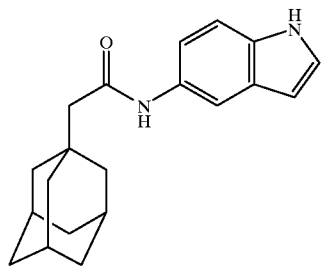

Prepared according to the method of Example 1b) from 1-adamantaneacetyl chloride (0.076 g) and 5-aminoindole (0.05 g) to give the title compound as a white solid (0.05 g).

Melting point: 184–185° C.; MS (APCI+ve) 309 (M+H)$^+$; $^1$H NMR (DMSO-d$_6$) δ 10.95 (1H, s), 9.51 (1H, s), 7.85 (1H, s), 7.28 (2H, m), 7.16 (1H, dd), 6.35 (1H, t), 2.04 (2H, s), 1.94 (3H, s), 1.70–1.50 (12H, m).

EXAMPLE 8

N-(2,3-Dimethyl-5-indolyl)-tricyclo[3.3.1.1$^{3,7}$]decane-1-acetamide

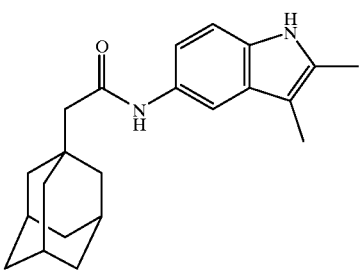

To a solution of 1-adamantaneacetic acid (0.30 g) in dichloromethane (10 ml) were added 4-dimethylaminopyridine (0.19 g) and 1-(3-dimethylaminopropyl)-3-ethylcarbodiimide hydrochloride (0.30 g). The reaction mixture was stirred for 0.5 hour before addition of 5-amino-2,3-dimethylindole (0.25 g). Stirring was then continued overnight at ambient temperature. The next day the reaction mixture was washed with dilute hydrochloric acid, water and brine, dried over sodium sulphate ($Na_2SO_4$) and finally concentrated under reduced pressure to leave a residue. Purification of the residue by silica gel chromatography, eluting with 40% ethyl acetate in isohexanes, gawe the title compound as a white solid (0.14 g).

Melting point: 234–235° C.; MS (APCI+ve) 337 (M+H)$^+$; $^1$H NMR (DMSO-$d_6$) δ 10.50 (1H, s), 9.46 (1H, s), 7.67 (1H, s), 7.08 (2H, m), 2.28 (3H, s), 2.03 (3H, s), 1.99 (2H, s), 1.94 (3H, s), 1.70–1.50 (12H, m).

EXAMPLE 9

N-[5-(3-N,N-Dimethylaminopropoxy)-2-methylphenyl]-tricyclo[3.3.1.1$^{3,7}$]decane-1-acetamide, hydrochloride

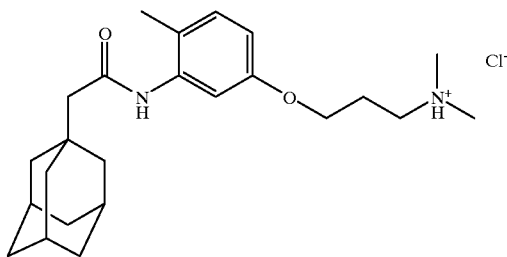

To a solution of N-(5-methoxy-2-methylphenyl)-tricyclo[3.3.1.1$^{3,7}$]decane-1-acetamide prepared as described in Example 5 (1.00 g) in dichloromethane (20 ml) was added borontribromide (4 ml of a 1.0M solution in dichloromethane) at –78° C. under an inert atmosphere. The reaction mixture was stirred for 24 hours and then warmed to ambient temperature and washed with brine. The organic layer was then dried over magnesium sulphate (MgSO$_4$) and concentrated under reduced pressure to yield a residue. To a solution of the residue (200 mg) in N,N-dimethylformamide (10 ml) were added potassiumn carbonate (0.185 g) and N,N-dimethyl-3-chloropropylamine hydrochloride (0.11 g) and the reaction mixture was heated, with stirring, to 80° C. for 4 hours. Once cooled, the reaction mixture was diluted with ethyl acetate and washed with saturated brine. The organic phase was separated, dried over magnesium sulphate (MgSO$_4$) and then passed through an "ISOLUTE" (trade mark) NH$_2$ solid phase extraction cartridge, eluting with ethyl acetate. Evaporation of the eluant, followed by treatment with 1.0M hydrogen chloride in ether and finally concentration under reduced pressure gave the title compound as a white solid (0.02 g).

Melting point: 139–140° C.; MS (APCI+ve) 385 (M+H)$^+$ (for free base); $^1$H NMR (DMSO-$d_6$) δ 10.38 (1H, s), 9.05 (1H, s), 7.08 (2H, d+s), 3.95 (4H, m), 3.2 (2H, m), 2.78 (6H, 2s), 2.13 (3H, s), 2.10 (2H, s), 1.95 (3H, s), 1.6 (12H,m).

EXAMPLE 10

N-(5-Indazolyl)-tricyclo[3.3.1.1$^{3,7}$]decane-1-acetamide

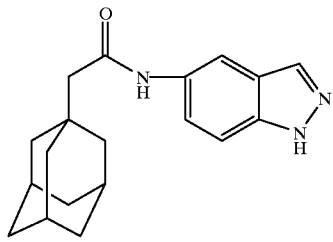

Prepared according to the method of Example 1b) from 1-adamantaneacetyl chloride (0.1 g) and 5-aminoindazole (0.067 g) to give the title compound as a white solid (0.12 g).

Melting point: 265° C.; MS (APCI+ve) 310 (M+H)$^+$; $^1$H NMR (DMSO-$d_6$) δ 12.93 (1H, s), 9.73 (1H, s), 8.12 (1H, s), 7.99 (1H, s), 7.40 (2H, m), 2.04 (2H, s), 1.94 (3H, s), 1.70–1.50 (12H, m).

EXAMPLE 11

N-(6-Indazolyl)-tricyclo[3.3.1.1$^{3,7}$]decane-1-acetamide

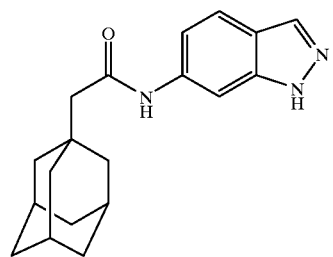

Prepared according to the method of Example 1b) from 1-adamantaneacetyl chloride (0.2 g) and 6-aminoindazole (0.13 g) to give the title compound as a white solid (0.064 g).

Melting point: 245° C.; MS (APCI+ve) 310 (M+H)$^+$; $^1$H NMR (DMSO-$d_6$) δ 12.84 (1H, s), 9.87 (1H, s), 8.16 (1H, s), 7.94 (1H, s), 7.62 (1H, d), 7.05 (1H dd), 2.04 (2H, s), 1.94 (3H, s), 1.70–1.50 (12H, m).

EXAMPLE 12

N-(5-Hydroxy-2-methylphenyl)-tricyclo[3.3.1.1$^{3,7}$]decane-1-acetamide

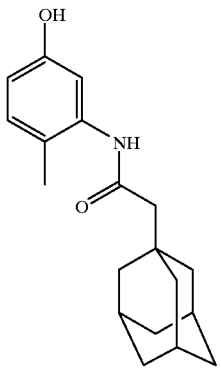

To a solution of N-(5-methoxy-2-methylphenyl)-tricyclo[3.3.1.1$^{3,7}$]decane-1-acetamide prepared as described in Example 5 (1.00 g) in dichloromethane (20 ml), was added boron tribromide (4 ml of a 1.0M solution in dichloromethane) at −78° C. under an inert atmosphere. The reaction mixture was stirred for 24 hours and then warmed to ambient temperature and washed with brine. The organic layer was dried over magnesium sulphate (MgSO$_4$) and concentrated under reduced pressure to yield a residue. Trituration with diethyl ether gave a solid (0.335 g). A portion of this material (0.050 g) was further purified by Supercritical Fluid chromatography using a Cyano column, eluting with a gradient of methanol in supercritical carbon dioxide to give the title compound as a white solid (0.030 g).

Melting point: 255–256° C.; MS (APCI+ve) 300 (M+H)$^+$; $^1$H NMR (DMSO-d$_6$) δ 9.11 (1H, s), 8.92 (1H, s), 6.92 (1H, m), 6.45 (1H,dd), 2.04 (5H, s), 1.94 (3H, s), 1.70–1.50 (12H, m).

EXAMPLE 13

N-(1H-Indol-4-yl)-tricyclo[3.3.1.1$^{3,7}$]decane-1-acetamide

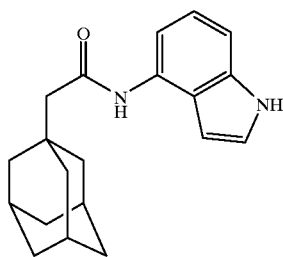

Prepared according to the method of Example 1b) from 1-adamantaneacetyl chloride (0.074 g) and 4-aminoindole hydrochloride (0.059 g) to give the title compound as a white solid (0.068 g).

Melting point: 211–213° C.; MS (APCI+ve) 309 (M+H)$^+$; $^1$HNMR (DMSO-d$_6$) δ 11.07 (1H, s), 9.35 (1H, s), 7.53 (1H, d), 7.27 (1H, t), 7.12 (1H, d), 6.99 (1H, t), 6.66 (1H, s), 2.19 (2H, s), 1.94 (3H, s), 1.68 (6H, d), 1.68–1.58 (6H, m).

EXAMPLE 14

4-Methyl-3-[[1-oxo-2-(tricyclo[3.3.1.1$^{3,7}$]dec-1-yl)ethyl]amino]phenoxy-acetic acid, hydrochloride salt

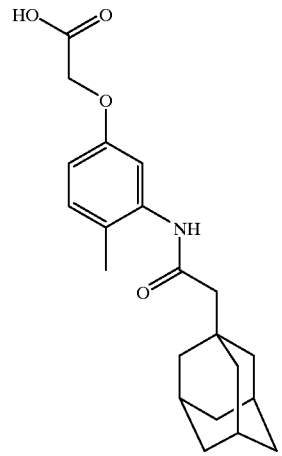

To a solution of N-(5-Hydroxy-2-methylphenyl)-tricyclo[3.3.1.1$^{3,7}$]decane-1-acetamide from Example 12 (0.20 g) was added potassium carbonate (0.106 g) and ethyl bromoacetate (0.3 ml). The reaction mixture was stirred and heated at 80° C. for 24 hours. Once cooled, the reaction mixture was diluted with ethyl acetate and washed with saturated brine. The organic phase was separated, dried over magnesium sulphate (MgSO$_4$) and evaporated under reduced pressure to leave a residue which was purified by silica gel chromatography eluting with iso-hexane/diethyl ether (1:1) to give a white solid. The solid was dissolved in dioxane (20 ml) and the solution treated with 2M sodium hydroxide solution, the reaction mixture was stirred at ambient temperature for 24 hours, acidified (2M hydrochloric acid) and extracted into ethyl acetate. The organic phase was washed with brine, dried over magnesium sulphate (MgSO4) and evaporated under reduced pressure. The residue was triturated with diethyl ether to leave the title compound as a white solid (0.070 g).

Melting point: 204–205° C.; MS (APCI+ve) 358 (M+H)$^+$; $^1$H NMR (DMSO-d$_6$) δ 12.95 (1H, s), 9.03 (1H, s), 7.05 (2H, m), 6.60 (1H,dd), 4.58 (2H, s), 2.12 (3H, s), 2.090 (2H, s), 1.94 (3H, s), 1.70–1.50 (12H, m).

EXAMPLE 15

N-(1-Methyl-1H-indol-5-yl)-tricyclo[3.3.1.1$^{3,7}$]decane-1-acetamide

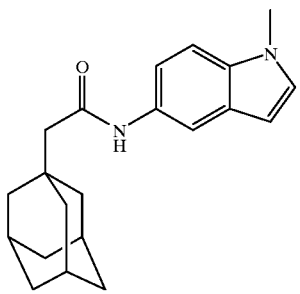

a) 1-Methyl-5-nitro-1H-indole

To a solution of 5-nitroindole (0.20 g) in tetrahydrofuran (2 ml) was added sodium hydride (0.06 g of 60% dispersion in oil) and evolution of gas noted. After stirring for 30 min methyl iodide (0.086 ml) was added to the dark brown reaction mixture and the reaction mixture heated to 65° C. for 2 hr before cooling to room temperature and partitioning between dichloromethane and water. Organic phase separated, washed with sodium thiosulphate solution, dried (Na$_2$SO$_4$) and concentrated to leave sub-title compound as a yellow solid (0.20 g). $^1$H NMR (DMSO-d$_6$) δ 8.58 (1H, d), 8.04 (1H, dd), 7.65 (1H, d), 7.61 (1H, d), 6.75 (1H, dd), 3.88 (3H, s).

b) N-(1-Methyl-1H-indol-5-yl)-tricyclo[3.3.1.1$^{3,7}$]decane-1-acetamide

To a solution of 1-methyl-5-nitroindole from step a) (0.11 g) in ethanol (10 ml) was added 10% palladium on carbon (0.023 g) and resulting suspension stirred under 4 bar pressure of hydrogen for 0.75 h before filtering off the catalyst and concentration at reduced pressure. The resulting residue was condensed with 1-adamantneacetyl chloride (0.10 g) according to the method of Example 1b) to give the title compound as a white solid (0.11 g).

Melting point: 183–184° C.; MS (APCI+ve) 323 (M+H)$^+$; $^1$H NMR (DMSO-d$_6$) δ 9.55 (1H, s), 7.87 (1H, d), 7.32 (1H, d), 7.26 (1H, d), 7.23 (1H, dd), 6.34 (1H, dd), 3.75 (3H, s), 2.04 (2H, s), 1.94 (3H, s), 1.75–1.50 (12H, m).

EXAMPLE 16

N-(1-(N,N-Dimethylaniino)ethyl-1H-indo-5-yl)-tricyclo[3.3.1.1$^{3,7}$]decane-1-acetamide

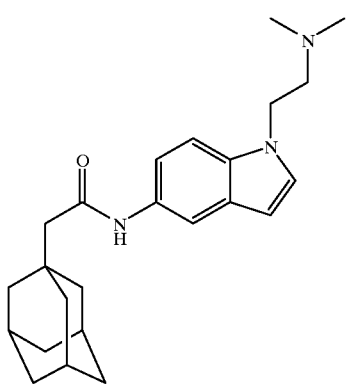

a) 1-(N,N-Dimethylamino)ethyl-5-nitro-1H-indole

Prepared according to the method of Example 15a) from 5-nitroindole (0.217 g) and dimethylaminoethyl chloride hydrochloride (0.21 g) to leave sub-title compound as an orange/brown solid (0.24 g).

$^1$H NMR (DMSO-d$_6$) δ 8.56 (1H, d), 8.02 (1H, dd), 7.71 (1H, d), 7.61 (1H, d), 6.74 (1H, dd), 4.35 (2H, t), 2.62 (2H, t), 2.17 (6H, s).

b) N-(1-(N,N-Dimethylamino)ethyl-1H-indo-5-yl)-tricyclo[3.3.1.1$^{3,7}$]decane-1-acetamide Prepared according to the method of Example 15b) from 1-(N,N-dimethylamino)ethyl-5-nitroindole (0.23 g) and 1-adamantaneacetyl chloride (0.21 g) to give the title compound as a white solid (0.22 g).

Melting point: 125–127° C.; MS (APCI+ve) 380 (M+H)$^+$; $^1$H NMR (DMSO-d$_6$) δ 9.54 (1H, s), 7.85 (1H, d), 7.36 (1H, d), 7.32 (1H, d), 7.20 (1H, dd), 6.33 (1H, d), 4.20 (2H, t), 2.58 (2H, t), 2.17 (6H, s), 2.04 (2H, s), 1.94 (3H, s), 1.65 (12H, m).

EXAMPLE 17

5-[[1-Oxo-2-(tricyclo[3.3.1.1$^{3,7}$]dec-1-yl)ethyl]amino]-1H-indole-1-acetic acid, 1,1-dimethylethyl ester

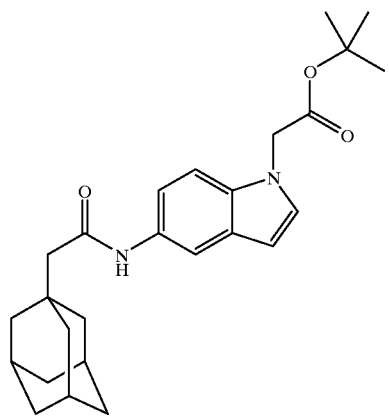

a) 5-Nitro-1H-indole-1-acetic acid, 1,1-dimethylethyl ester

Prepared according to the method of Example 15a) from 5-nitroindole (0.207 g) and 2-bromoaceticacid, 1,1-diemthylethyl ester (0.23 ml) to leave sub-title compound as a yellow oily solid (0.29 g).

$^1$H NMR (DMSO-d$_6$) δ 8.58 (1H, d), 8.04 (1H, dd), 7.60 (2H, m), 6.77 (1H, dd), 3.15 (2H, s), 1.42 (9H, s).

b) 5-[[1-Oxo-2-(tricyclol3.3.1.1$^{3,7}$]dec-1-yl)ethyl]amino]-1H-indole-1-acetic acid, 1,1-dimethylethyl ester Prepared according to the method of Example 15b) from 5-nitro-1H-indole-1-acetic acid, 1,1-dimethylethyl ester (0.29 g) and 1-adamantaneacetyl chloride (0.20 g) to give the title compound as a white solid (0.24 g).

Melting point: 199° C.; MS (APCI+ve) 423 (M+H)$^+$; $^1$H NMR (DMSO-d$_6$) δ 9.56 (1H, s), 7.86 (1H, d), 7.27 (1H, d), 7.22 (2H, m), 6.38 (1H, d), 4.94 (2H, s), 2.04 (2H, s), 1.94 (3H, s), 1.65 (12H, m), 1.41 (9H, s).

EXAMPLE 18

N-(3-(2-Chloropyridyl))-tricyclo[3.3.1.1$^{3,7}$]decane-1-acetanide

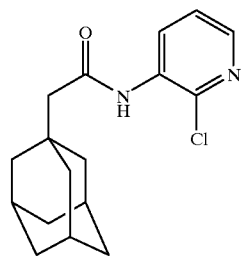

Prepared according to the method of Example 1b) from 1-adamantaneacetyl chloride (0.5 g) and 2-chloro-3-aminopyridine (0.31 g) to give the title compound as a white solid (0.27 g).

Melting point: 135–136° C.; MS (APCI+ve) 305 (M+H)$^+$; $^1$H NMR (DMSO-d$_6$) δ 9.51 (1H, s), 8.22 (1H, dd), 8.15 (1H, dd), 7.4 (1H, dd), 2.20 (2H, s), 1.98 (3H, s), 1.60 (12H, m).

EXAMPLE 19

N-(3-(N,N-Dimethylamiino)methyl-1H-indo-5-yl)-tricyclo[3.3.1.1$^{3,7}$]decane-1-acetamide

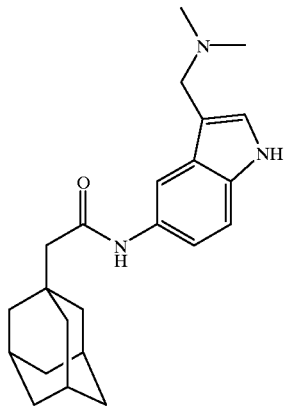

To a suspension of indole amide from Example 7 (0.163 g) in acetic acid (0.20 ml) was added aqueous dimethylamine (0.065 ml of a 40% solution), aqueous formaldehyde (0.043 ml of a 37% solution) and acetic acid (0.10 ml) and resulting reaction mixture heated to 60° C. for 2 hr before cooling to 0–5° C. Reaction mixture made alkaline by addition of aqueous ammonia solution and partitioned between ethyl acetate and water. Organic phase separated, washed with brine, dried (Na$_2$SO$_4$) and concenetrated and residue purified by chromatography on Al$_2$O$_3$ eluting with 0–10% methanol in dichloromethane to give the title compound as a brown solid (0.07 g).

Melting point: 194–213° C. (dec.); MS (APCI+ve) 366 (M+H)$^+$; $^1$H NMR (DMSO-d$_6$) δ 11.24 (1H, s), 9.62 (1H, s), 8.00 (1H, s), 7.46 (1H, d), 7.32 (1H, d), 7.21 (1H, dd), 4.12 (2H, br s), 2.55 (6H, s), 2.06 (2H, s), 1.94 (3H, s), 1.70–1.58 (12H, m).

EXAMPLE 20

N-(4-Methoxy-2-methylphenyl)-tricyclo[3.3.1.1$^{3,7}$]decane-1-acetamide

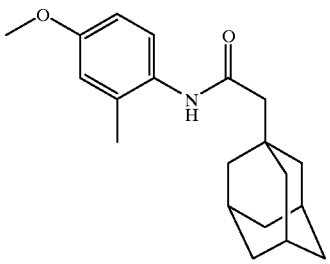

Prepared according to the method of Example 1b) from 1-adamantaneacetyl chloride (2.0 g) and 4-methoxy-2-methylaniline (1.29 g) to give the title compound as a white solid (1.37 g).

Melting point: 156–157° C.; MS (APCI+ve) 314 (M+H)$^+$; $^1$H NMR (DMSO-d$_6$) δ 9.01 (1H, s), 7.15 (1H, d), 6.80 (1H, d), 6.7 (1H, dd), 3.7 (3H, s), 2.20 (3H, s), 2.05 (2H, s), 1.95 (3H, s), 1.60 (12H, m).

EXAMPLE 21

N-(2-Chloro-5-methoxyphenyl)-tricyclo[3.3.1.1$^{3,7}$]decane-1-acetaide

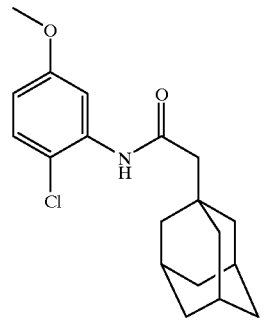

Prepared according to the method of Example 1b) from 1-adamantaneacetyl chloride (2.0 g) and 2-chloro-5-methoxyaniline (1.49 g) to give the title compound as a white solid (0.60 g).

Melting point: 122–123° C.; MS (APCI+ve) 334 (M+H)$^+$; $^1$H NMR (DMSO-d$_6$) δ 9.20 (1H, s), 7.36 (2H, m), 6.76 (1H, dd), 6.7 (1H, dd), 3.73 (3H, s), 2.20 (2H, s), 1.95 (3H, s), 1.60 (12H, m).

EXAMPLE 22

N-(4-Hydroxy-2-methylphenyl)-tricyclo[3.3.1.1$^{3,7}$]decane-1-acetamiide

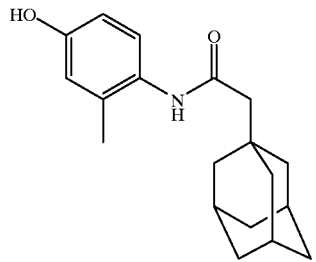

To a solution of N-(4-Methoxy-2-methylphenyl)-tricyclo[3.3.1.1$^{3,7}$]decane-1-acetamide from Example 20 (1.20 g) in dichloromethane (50 ml) at −78° C. was added boron tribromide (4 ml of a 1.0M solution in dichloromethane) under an inert atmosphere. The reaction mixture was stirred for 24 hours and then warmed to ambient temperature and washed with brine. The organic layer was then dried over magnesium sulphate (MgSO$_4$) and concentrated under reduced pressure to yield a residue which was purified by silica gel chromatography eluting with iso-hexane/diethyl ether (1:1) to give the ititle compound as a white solid. (0.54 g).

Melting point: 205–206° C.; MS (APCI+ve) 300 (M+H)$^+$; $^1$H NMR (DMSO-d$_6$) δ 9.15 (1H, s), 8.91 (1H, s), 7.00 (1H, d), 6.54 (2H, m), 2.53 (3H, s), 2.03 (2H, s), 1.94 (3H, s), 1.70–1.50 (12H, m).

EXAMPLE 23

N-(3-Hydroxymethyl-2-methylphenyl)-tricyclo[3.3.1.1$^{3,7}$]decane-1-acetamide

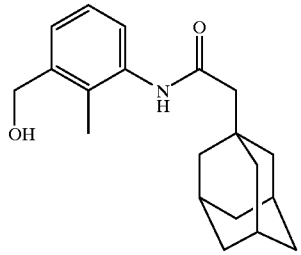

Prepared according to the method of Example 1b) from 1-adamantaneacetyl chloride (2.0 g) and 3-amino-2-methylbenzyl alcohol (1.29 g). Silica gel chromatography, eluting with 5% ethylacetate in dichloromethane gave the title compound as a white solid (0.80 g).

Melting point: 205–206° C.; MS (APCI+ve) 314 (M+H)$^+$; $^1$H NMR (DMSO-d$_6$) δ 9.16 (1H, s), 7.20–7.05 (3H, m), 5.07 (1H, bs), 4.47 (2H, s), 2.09 (2H, s), 2.08 (3H, s), 1.95 (3H, s), 1.60 (12H, m).

EXAMPLE 24

N-(5-Methoxy-2-methyl-3-nitrophenyl)-tricyclo[3.3.1.1$^{3,7}$]decane-1-acetamide

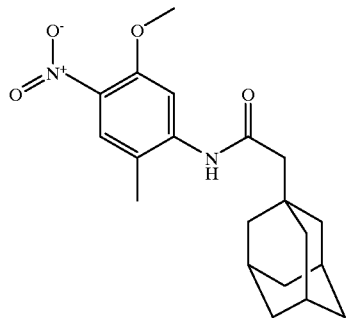

Prepared according to the method of Example 1b) from 1-adamantaneacetyl chloride (2.0 g) and 5-methoxy-2-methyl-4-nitroaniline (1.71 g). Silica gel chromatography, eluting with iso-hexane/diethyl ether (1:1), gave the title compound as a yellow solid (1.10 g).

Melting point: 141–142° C.; MS (APCI+ve) 359 (M+H)$^+$; $^1$H NMR (DMSO-d$_6$) δ 9.26 (1H, s), 7.82 (1H, s), 7.76 (1H, s), 3.86 (3H, s), 2.23 (3H, s), 2.08 (2H, s), 1.95 (3H, s), 1.60 (12H, m).

EXAMPLE 25

N-(5-Hydroxymethyl-2-methylphenyl)-tricyclo[3.3.1.1$^{3,7}$]decane-1-acetamide

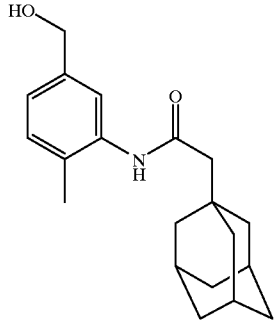

Prepared according to the method of Example 1b) from 1-adamantaneacetyl chloride (2.0 g) and 3-amino4-methylbenzyl alcohol (1.29 g). Silica gel chromatography, eluting with 5% ethylacetate in dichloromethane gave the title compound as a white solid (1.10 g).

Melting point: 190° C.; MS (APCI+ve) 314 (M+H)$^+$; $^1$H NMR (DMSO-d$_6$) δ 8.54 (1H, bs), 7.46 (1H, s), 7.1 (2H, m), 4.70 (1H, bs), 4.54 (2H, d), 2.24 (3H, s), 2.15 (2H, s), 2.0 (3H, s), 1.70 (12H, m).

EXAMPLE 26

N-(3-Hydroxy-2-methylphenyl)-tricyclo[3.3.1.1$^{3,7}$]decane-1-acetamide

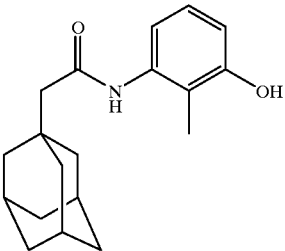

Prepared according to the method of Example 1b) from 1-adamantaneacetyl chloride (0.81) and 3-amino-2-methylphenol (0.5 g) to give the title compound as a white solid (0.5 g).

Melting point: 211° C.; MS (APCI+ve) 300 (M+H)$^+$; $^1$H NMR (DMSO-d$_6$) δ 9.28 (1H, bs), 9.04 (1H, bs), 6.91 (1H, t), 6.8 (1H, d), 6.6 (1H, d, ), 2.05 (2H, s), 1.98 (3H, S) 1.94 (3H, bs), 1.6 (12H, m).

EXAMPLE 27

N-(2-Methyl-5-(1-pyrrolidinemethyl)phenyl)-tricyclo[3.3.1.1^{3,7}]decane-1-acetamide, hydrochloride

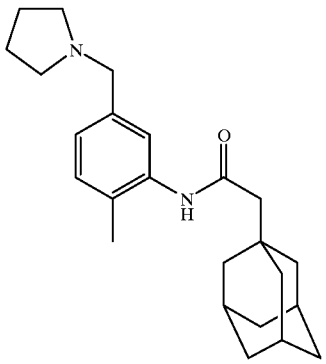

To a solution of N-(5-Hydroxymethyl-2-methylphenyl)-tricyclo[3 3.1.1^{3,7}]decane-1-acetamide from Example 25) (1.0 g) in acetonitrile was added triphenylphosphine (0.93 g) and carbon tetrabromide (1.2 g). The reaction mixture was stirred at ambient temperature for 24 hours and evaporated under reduced pressure. The residue was purified by silica gel chromatography eluting with iso-hexane/diethyl ether to give a white solid. A portion (0.1 g) of the solid was dissolved in acetonitrile (3 ml) and treated with pyrrolidine (0.2 ml). The reaction mixture was stirred and heated at 80° C. for 24 hours. Once cooled, the reaction mixture was diluted with ethyl acetate and washed with saturated brine. The organic phase was separated, dried over magnesium sulphate ($MgSO_4$), treated with a solution of hydrogen chloride in diethyl ether (1 ml of 1.0M) and evaporated under reduced pressure to leave a residue which was triturated with iso-hexane to give the title compound as an off-white solid. (0.030 g).

Melting point: 214–215° C.; MS (APCI+ve) 367 (M+H)+ for free base. $^1$H NMR (DMSO-$d_6$) δ 9.22 (1H, s), 7.60 (1H, s), 7.27(2H, s), 4.27 (2H, d), 3.35 (2H, m), 3.05 (2H, m), 2.21 (3H, s), 2.1 (2H, s), 2.0–1.8 (7H, m), 1.60 (12H, m).

EXAMPLE 28

N-(2-Chloro-5-hydroxyphenyl)-tricyclo[3.3.1.1^{3,7}]decane-1-acetamide

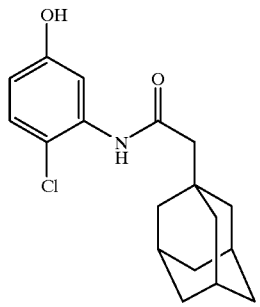

Prepared according to the method of Example 1b) from 1-adamantaneacetyl chloride (2.9 g) and 2-chloro-4-hydroxyaniline (2.0 g). Silica gel chromatography, eluting with 30% diethyl ether in iso-hexane, followed by recrystallisation from acetonitrile gave the title compound as a white solid (0.15 g).

Melting point: 224–225° C.; MS (APCI+ve) 320 (M+H)+; $^1$H NMR (DMSO-$d_6$) δ 9.76(1H, s), 9.14 (1H, s), 7.26 (1H, d), 6.83 (1H, d), 6.69 (1H, dd), 2.05 (2H, s), 1.95 (3H, s), 1.60 (12H, m).

EXAMPLE 29

N-(2-Chloro-4-hydroxyphenyl)-tricyclo[3.3.1.1^{3,7}]decane-1-acetamide

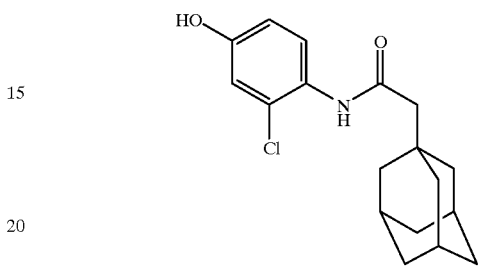

Prepared according to the method of Example 1b) from 1-adamantaneacetyl chloride (2.9 g) and 2-chloro-4-hydroxyaniline to give the title compound as a white solid. (0.15 g).

Melting point: 224–225° C.; MS (APCI+ve) 320 (M+H)+; $^1$H NMR (DMSO-$d_6$) δ 9.65 (1H, s), 9.09 (1H, s), 7.23 (2H, m), 6.55 (1H, dd), 2.20 (2H, s), 1.95 (3H, s), 1.60 (12H, m).

EXAMPLE 30

N-(2-Methyl-3-(2-(1-pyrrolidino)ethyloxy)phenyl)-tricyclo[3.3.1.1^{3,7}]decane-1-acetamide, hydrochloride

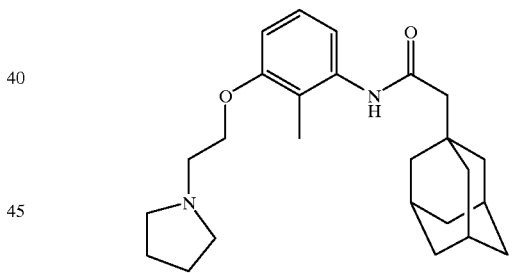

To a solution of N-(3-Hydroxy-2-methylphenyl)-tricyclo [3.3.1.1^{3,7}]decane-1-acetamide from Example 26 (0.060 g), in acetonitrile (3 ml), was added caesium carbonate (0.196 g) and N-(2-chloroethyl)-pyrrolidine hydrochloride (0.068 g). The reaction mixture was stirred and heated at 80° C. for 24 hours. After cooling, the reaction mixture was diluted with ethyl acetate and washed with water. The organic phase was dried over magnesium sulphate and evaporated under reduced pressure to leave a residue which was purified by Supercritical Fluid Chromatography using a gradient elution of 0.1% v/v solution of diethylamine in methanol and supercritical carbon dioxide on a Cyano column. The pure product was dissolved in dichloromethane, treated with 1.0M solution of hydrogen chloride in diethyl ether and evaporated under reduced pressure to leave the title compound as a white solid. (0.010 g).

Melting point: 105–106° C.; MS (APCI+ve) 397 (M+H)+ for free base. $^1$H NMR (DMSO-$d_6$) δ 9.22 (1H, s), 7.12 (1H, t), 6.97 (1H, d), 6.81 (1H, d), 4.30 (2H, t), 3.60 (4H, m), 3.10 (2H, m), 2.05 (6H, s), 1.95 (6H, m), 1.60 (12H, m).

EXAMPLE 31

N-(5-Methoxymethyl2-methylphenyl)-tricyclo[3.3.1.1$^{3,7}$]decane-1-acetamide

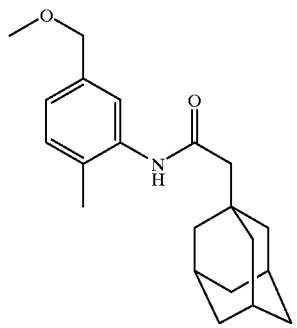

To a solution of the benzyl bromide prepared in Example 27 (0.10 g) in methanol (5 ml) and added sodium methoxide (0.020 g). The reaction mixture was stirred at ambient temperature for 2 hours then evaporated under reduced pressure to leave a residue which was dissolved in ethyl acetate and washed with 2M hydrochloric acid. The organic phase was dried over magnesium sulphate and evaporated under reduced pressure, the residue was triturated with diethyl ether to yield the title compound as a white solid. (0.015 g).

Melting point: 127–128° C.; MS (APCI+ve) 328 (M+H)$^+$; $^1$H NMR (DMSO-d$_6$) δ 9.10 (1H, s), 7.33 (1H, s), 7.15 (1H, d), 6.99 (1H, d), 4.34 (2H, s), 2.20 (3H, s), 2.10 (2H, s), 1.95 (6H, m), 1.60 (12H, m).

EXAMPLE 32

N-(2-Methyl-3-(2-(1-morpholino)ethyloxy)phenyl)-tricyclo[3.3.1.1$^{3,7}$]decane-1-acetamide, hydrochloride

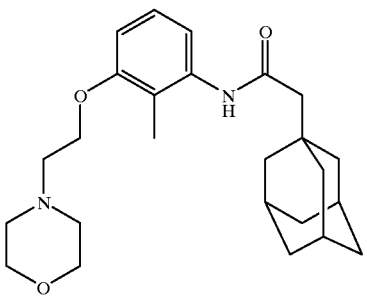

Prepared according to the method of Example 30 from N-(3-Hydroxy-2-methylphenyl)-tricyclo[3.3.1.1$^{3,7}$]decane-1-acetamide (0.060 g) and N-(2-chloroethyl)-morpholine hydrochloride (0.075 g) to give the title compound as a white solid. (0.024 g).

Melting point: 195–197° C.; MS (APCI+ve) 413 (M+H)$^+$ for free base. $^1$H NMR (DMSO-d$_6$) δ 11.36 (1H, bs), 9.23 (1H, s), 7.15 (1H, t), 6.99 (1H, d), 6.83 (1H, d), 4.42 (2H, t), 4.10–3.0 (12H, m), 2.08 (2H, s), 2.07 (3H, s), 1.95 (3H, s), 1.60 (12H, m).

EXAMPLE 33

N-(2-Methyl-3(2-(1-piperidino)ethyloxy)phenyl)-tricyclo[3.3.1.1$^{3,7}$]decane-1-acetamide, hydrochloride

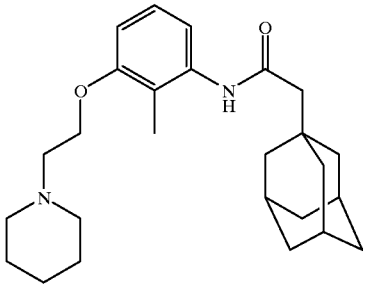

Prepared according to the method of Example 30 from N-(3-Hydroxy-2-methylphenyl)-tricyclo[3.3.1.1$^{3,7}$]decane-1-acetamide (0.060 g) and N-(2-chloroethyl)-piperidine hydrochloride (0.074 g) to give the title compound as a white solid (0.036 g).

Melting point: 105–106° C.; MS (APCI+ve) 412(M+H)$^+$ for free base. $^1$H NMR (DMSO-d$_6$) δ 10.62 (1H, bs), 9.24 (1H, s), 7.12 (1H, t), 6.97 (1H, d), 6.82 (1H, d), 4.42 (2H, t), 3.50 (4H, m), 3.05 (2H, m), 2.10 (2H, s), 2.05 (3H, s), 2.0 (3H, s), 1.90–1.50 (18H, m).

EXAMPLE 34

N-(2-Methyl-5-(1-morpholinomethyl)phenyl)-tricyclo[3.3.1.1$^{3,7}$]decane-1-acetamide, hydrochloride

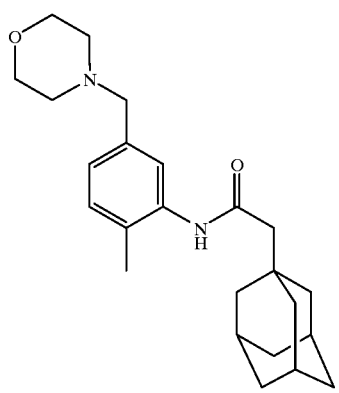

Prepared according to the method of Example 27 from N-(5-Hydiroxymethyl-2-methylphenyl)-tricyclo[3.3.1.1$^{3,7}$]decane-1-acetamide and morpholine hydrochloride (0.040 ml). Purification by Supercritical Fluid chromatography using a gradient elution of 0.1% v/v solution of diethylamine in methanol and supercritical carbon dioxide on a Cyano column gave the pure product which was dissolved in dichloromethane, treated with 1.0M solution of hydrogen chloride in diethyl ether and evaporated under reduced pressure to leave the title compound as a white solid (0.085 g).

Melting point: 204–205° C.; MS (APCI+ve) 384 (M+H)$^+$ for free base. $^1$H NMR (DMSO-d$_6$) δ 9.22 (1H, s), 7.60 (1H, s), 7.27 (2H, s), 4.30 (2H, d), 4.0 (2H, m), 3.8–3.6 (4H, m), 3.40–2.8 (7H, m), 2.25 (3H, s), 2.15 (2H, s), 2.0 (3H, s), 1.60 (12H, m).

EXAMPLE 35

N-(5-(3-(2-N,N-dimethylaminoethyl)indolyl))-tricyclo[3.3.1.1$^{3,7}$]decane-1-acetamide, hydrochloride

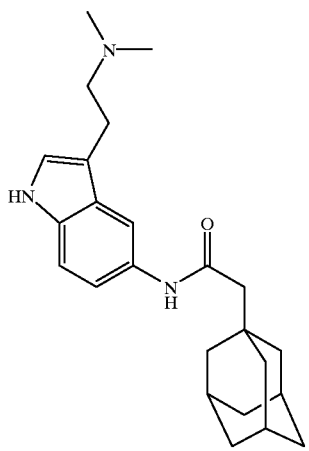

Prepared according to the method of Example 1b) from 1-adamantaneacetyl chloride (0.040 g) and 5-amino-3-(2-dimethylaminoethylindole dihydrochloride (0.18 g). Supercritical Fluid chromatography using a gradient elution of 0.1% v/v solution of diethylamine in methanol and supercritical carbon dioxide on a Cyano column gave the pure product which was dissolved in dichloromethane, treated with 1.0M solution of hydrogen chloride in diethyl ether and evaporated under reduced pressure to leave the title compound as a pale yellow solid. (0.031 g).

Melting point: 145–147° C.; MS (APCI+ve) 380 (M+H)$^+$ for free base. $^1$H NMR (DMSO-d$_6$) δ 10.89 (1H, s), 9.58 (1H, s), 7.95 (1H, d), 7.25 (1H, dd), 7.15 (1H, d), 7.12 (1H, dd), 3.33 (2H, m), 3.05 (2H, m), 2.85 (6H, 2s), 2.03 (2H, s), 1.95 (3H, s), 1.60 (12H, m).

EXAMPLE 36

Methyl 4-methyl-3-[[1-oxo-2-(tricyclo[3.3.1.1$^{3,7}$]dec-1-yl)ethyl]amino]thiophene-2-carboxylate

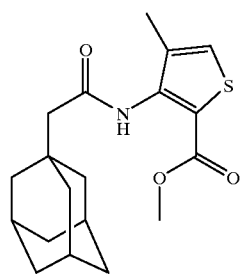

A solution of 1-adamantaneacetyl chloride (0.2 g) prepared as described in Example 1a) was added to a solution of methyl 3-amino-4-methylthiophene-2-carboxlate (0.16 g) in pyridine (2 ml) and dichloromethane (4 ml). The reaction mixture was stirred at ambient temperature for 2 days before being diluted with ethyl acetate. The organic phase was then washed with dilute hydrochloric acid and water, dried over magnesium sulphate (MgSO$_4$) and finally concentrated under reduced pressure to give an oil. Purification of the residue by silica gel chromatography, eluitng with 10% ethyl acetate in isohexanes, gave the title compound as a white solid (0.049 g).

Melting point: 124–124.5° C.; MS (APCI+ve) 348 (M+H)$^+$; $^1$H NMR (CDCl$_3$) δ 8.76 (1H, s), 7.13(1H, s), 3.86 (3H, s), 2.23 (3H, s), 2.18 (2H, s), 2.0 (3H, bs), 1.70 (12H, m).

EXAMPLE 37

N-(3-Methoxy-2-methylphenyl)-tricyclo[3.3.1.1$^{3,7}$]decane-1-acetamide

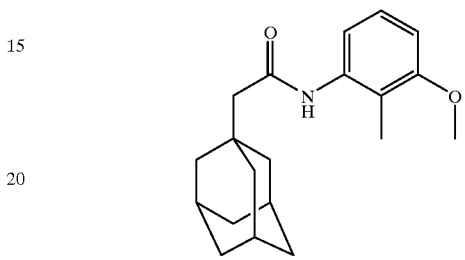

Diethyl azodicarboxylate (0.20 ml) was added to a solution of N-(3-hydroxy-2-methylphenyl)-tricyclo[3.3.1.1$^{3,7}$]decane-1-acetamide (0.20 g, Example 26), methanol (0.10 ml) and triphenylphosphine (0.41 g) in toluene (10 ml) and tetrahydrofuran (5 ml). After 2 hours stirring at room temperature further triphenylphosphine (0.20 g) and diethyl azodicarboxylate (0.10 ml) were added and the solution stirred for 2 hours. The reaction mixture was concentrated under reduced pressure and the residue purified by silica gel to chromatography eluting with dichloromethane:ethyl acetate (19:1) to give the title compound as a colourless solid (0.20 g).

Melting point: 173–175° C.; MS (APCI+ve) 314 (M+H)$^+$; $^1$H NMR (CDCl$_3$) δ 7.48 (1H, d), 7.16 (1H, t), 6.86 (1H, bs), 6.69 (1H, d), 3.82 (3H, s), 2.13 (5H, s), 2.00 (3H, s), 1.75–1.6 (12H, m).

EXAMPLE 38

N-(2-Methyl-3-(2-(1-imidazolo)ethyloxy)phenyl)-tricyclo[3.3.1.1$^{3,7}$]decane-1-acetamide

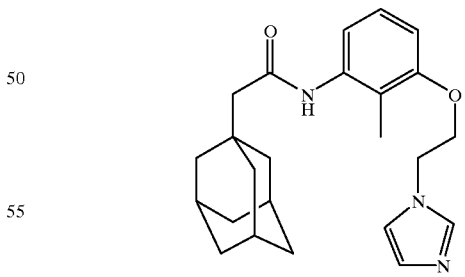

Diethyl azodicarboxylate (0.060 ml) was added to a solution of N-(3-hydroxy-2-methylphenyl)-tricyclo[3.3.1.1$^{3,7}$]decane-1-acetamide (0.100 g, Example 26), 1-(2-hydroxyetheyl)imidazole (0.048 g, J. Heterocyclic Chem., 1990, 27, 215) and triphenylphosphine (0.097 g) in tetrahydrofuran (4 ml). After 24 hours stirring at room temperature further triphenylphosphine (0.100 g) and diethyl azodicarboxylate (0.060 ml) were added and the solution stirred for 6 days. The reaction mixture was concentrated under reduced pressure and the residue purified by NPHPLC on a Novapak® column using a Gilson automated chromatography machine eluting with 0–10% ethanol in dichloromethane to give an oil which was triturated with ether to give the title compound as a colourless solid (0.041 g).

Melting point: 119.5–121° C.; MS (APCI+ve) 394 (M+H)$^+$; $^1$H NMR (CDCl$_3$) δ 7.60 (1H, s), 7.51 (1H, d), 7.14 (1H, t), 7.08 (1H, s), 7.03 (1H, s), 6.85 (1H, bs), 6.61 (1H, d), 4.37 (2H, t), 4.21 (2H, t), 2.13 (2H, s), 2.09 (3H, s), 2.00 (3H, s), 1–8–1.6 (12H, m).

EXAMPLE 39

N-(2,4,6-Trimethylphenyl)-tricyclo[3.3.1.1$^{3,7}$]decane-1-acetamide

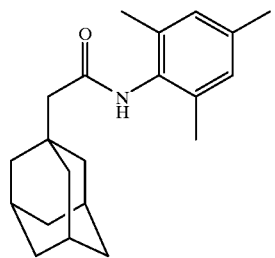

Thionyl chloride (3 ml) was added to 1-adamantaneacetic acid (0.50 g) and the reaction heated at reflux for 2 minutes. The excess thionyl chloride was removed by concentration under reduced pressure and the residue was dissolved in dichloromethane (5 ml). This solution was added to a solution of 2,4,6-trimethylaniline (0.72 ml) in dichloromethane (20 ml) and triethylamine (1 ml) at room temperature over 1 minute. After 5 minutes the reaction mixture was concentrated under reduced pressure and the residue added to a column of silica. The mixture was then chromatographed eluting with dichloromethane then dichloromethane:ethyl acetate (9:1) to give the title compound as a colourless solid (0.469 g).

Melting point: 212–215° C.; MS (APCI+ve) 312 (M+H)$^+$; $^1$H NMR (DMSO-d$_6$) δ 8.97 (1H, s), 6.85 (2H, s), 2.21 (3H, s), 2.10 (6H, s), 2.06 (2H, s), 1.95 (3H, s), 1.8–1.5 (12H, m).

EXAMPLE 40

N-(5-(3-Aminopropyloxy)-2-methylphenyl)-tricyclo[3.3.1.1$^{3,7}$]decane-1-acetamide, hydrochloride

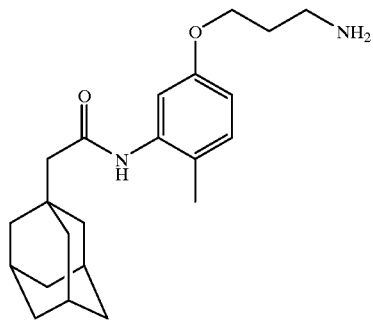

Prepared according to the method of Example 2 using diethyl azodicarboxylate (1.05 ml), N-(5-hydroxy-2-methylphenyl)-tricyclo[3.3.1.1$^{3,7}$]decane-1-acetamide (0.506 g, Example 12), tert-butyl N-(3-hydroxypropyl)carbamate (1.15 g) and tiphenylphosphine (1.75 g) to give the title compound as a yellow solid (0.21 g).

Melting point: 145° C. (dec.); MS (APCI+ve) 357 (M–HCl+H)$^+$; $^1$H NMR (DMSO-d$_6$) δ 9.05 (1H, s), 7.91 (3H, bs), 7.15–7.05 (2H, m), 6.66 (1H, dd), 3.99 (2H, t), 2.94 (2H, t), 2.13 (3H, s), 2.10 (2H, s), 2.05–1.9 (5H, m), 1.75–1.55 (12H, m).

EXAMPLE 41

N-(5-(3-(N-Methylamino)propyloxy)-2-methylphenyl)-tricyclo[3.3.1.1$^{3,7}$]decane-1-acetamide, hydrochloride

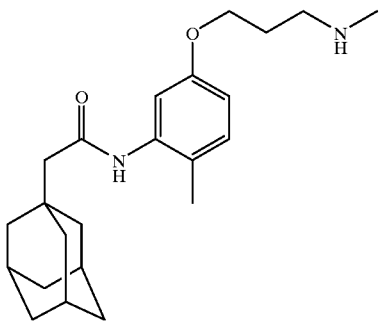

Diethyl azodicarboxylate (0.50 ml) was added to a solution of N-(5-hydroxy-2-methylphenyl)-tricyclo[3.3.1.1$^{3,7}$]decane-1-acetamide (0.50 g, Example 12), tert-butyl N-(3-hydroxypropyl)-N-methylcarbamate (0.60 g, J. Org. Chem., 1988, 53(10), 2229) and triphenylphosphine (0.88 g) in tetrahydrofuran (5 ml). After stirring for 19 hours at room temperature further triphenylphosphine (0.90 g) and diethyl azodicarboxylate (0.50 ml) were added. After stirring for 4 hours at room temperature further triphenylphosphine (0.90 g) and diethyl azodicarboxylate (0.50 ml) were added and the reaction mixture was stirred for 3 days. The reaction was then concentrated under reduced pressure and the residue was purified by silica gel chromatography eluting with dichloromethane:ethyl acetate (9:1) to give material that was further purified by chromatography over a Dynamax® column using a Gilson automated chromatography machine eluting with iso-hexane:ethyl acetate (4:1) to give the Mitsunobu reaction product (0.29 g) which was dissolved in methanol (10 ml). A solution of hydrogen chloride (generated by slow addition of acetyl chloride (12 ml) to methanol (10 ml) at 0° C. CARE—Very Exothermic) was then added to the latter solution and the reaction stirred at room temperature for 1 hour. The reaction was then concentrated under reduced pressure to give the title compound as a yellow solid (0.13 g).

MS (APCI+ve) 371 (M–HCl+H)$^+$; $^1$H NMR (DMSO-$_6$) δ 9.05 (1H, s), 8.76 (2H, bs), 7.15–7.05 (2H, m), 6.66 (1H, dd), 3.99 (2H, t), 3.1–2.95 (2H, m), 2.6–2.5 (3H, m), 2.13 (3H, s), 2.10 (2H, s), 2.1–2.0 (2H, m), 1.94 (3H, m), 1.75–1.55 (12H, m).

EXAMPLE 42

N6-(Tricyclo[3.3.1.1[3,7]]decane-1-acetyl)adenine

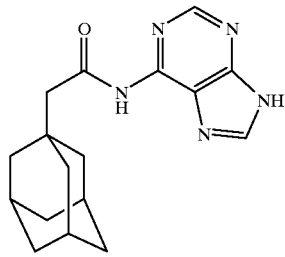

To a solution of 1-adamantaneacetyl chloride from Example 1a) (0.226 g) in dichloromethane (5 ml) was added 4-nitrophenol (0.149 g) and reaction mixture stirred at room temperature for 1 hr before concentration at reduced pressure. The resulting 4-nitrophenol ester was used without further purification.

To a suspension of the 4-nitrophenol ester (0.209 g), adenine (0.09 g) in dimethylsulphoxide (1.4 ml) was added triethylamine (0.19 ml) and reaction mixture heated to 90° C. for 2 days before cooling to room temperature. Reaction mixture was poured into aqueous sodium hydrogencarbonate solution and extracted with ethyl acetate. Organic extracts combined, washed with water (×3), brine, dried ($Na_2SO_4$) and concentrated at reduced pressure. Trituration of the residue with isohexane and ether left the product as a pale yellow solid (0.036 g).

Melting point: 309° C. (dec.); MS (APCI+ve) 312 (M+H)$^+$; $^1$H NMR (DMSO-$d_6$) δ 12.10 (1H, s), 11.06 (1H, s), 8.61 (1H, s), 8.40 (1H, s), 2.29 (2H, s), 1.92 (3H, s), 1.66 (6H, d), 1.60 (6H, m).

EXAMPLE 43

N-(3,5-Dimethoxy-2-methylphenyl)-tricyclo[3.3.1.1[3,7]]decane-1-acetamide

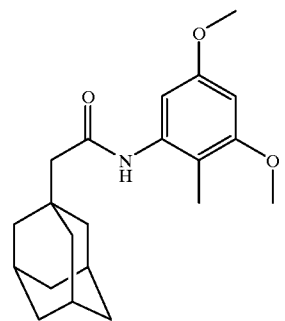

a) 3,5-Dimethoxy-2-methylbenzoic acid

To a solution of methyl 3,5-dimethoxy-2-methylbenzoate (5.83 g, J. C. S. Perkin I, 1973, 2853.) in methanol (80 ml) was added a solution of aqueous sodium hydroxide (10%, 80 ml) and reaction mixture stirred at room temperature for 1 hour. The reaction was then concentrated under reduced pressure to approximately half of the original volume before adding aqueous hydrochloric acid (200 ml). The white precipitate that formed was extracted with ethyl acetate (2×250 ml). The combined extracts were dried over anhydrous magnesium sulphate, filtered and concentrated under reduced pressure to give the sub-title compound as a colourless solid (5.41 g).

$^1$H NMR (CDCl$_3$) δ 7.10 (1H, d), 6.64 (1H, d), 3.84 (6H, s), 2.45 (3H, s).

b) N-(3,5-Dimethoxy-2-methylphenyl)-tricyclo[3.3.1.1[3,7]]decane-1-acetamide

Triethylamine (0.8 ml) followed by diphenylphosphoryl azide (1.2 ml) were added to a solution of 3,5-dimethoxy-2-methylbenzoic acid (1.0 g) in tert-butanol (30 ml) and the mixture was heated at reflux temperature for 12 hours. The reaction was cooled and concentrated under reduced pressure. The residue was partitioned beitween aqueous sodium hydroxide (2M, 100 ml)and dichloromethane (300 ml). The organic phase was dried over anhydrous sodium sulphate, filtered and concentrated under reduced pressure to give an oil (0.74 g) which was dissolved in methanol (10 ml). A solution of hydrogen chloride (generated by slow addition of acetyl chloride (12 ml) to methanol (10 ml) at 0° C. CARE—Very Exothermic) was then added to the latter solution and the reaction stirred at room temperature for 1 hour. The reaction was concentrated under reduced pressure and the residue partitioned between an aqueous solution of saturated sodium hydrogen carbonate (100 ml) and dichloromethane (100 ml). The organic phase was dried over magnesium sulphate, filtered and concentrated under reduced pressure to give an oil (0.5 g) which was dissolved in dichloromethane (10 ml) and triethylamine (2 ml). A solution of 1-adamantaneacetyl chloride (generated from 1-adamantaneacetic acid (0.50 g) andthionyl chloride) in dichloromethane (5 ml) was added to the latter solution and the mixture stirred at room temperature for 2 hours. The reaction was diluted with dichloromethane (100 ml) and the solution washed with aqueous hydrochloric acid (2M, 50 ml) then an aqueous solution of saturated sodium hydrogen carbonate (50 ml). The organi c phase was dried over anhydrous magnesium sulphate, filtered and concentrated under reduced pressure. The residue was purified by column chromatography over silica elutirng with dichloromethane then dichloromethane:ethyl acetate (19:1) to give the title compound as a colourless solid (0.54 g).

Melting point: 201–203° C.; MS (APCI+ve) 344 (M+H)$^+$; $^1$H NMR (DMSO-$d_6$) δ 9.08 (1H, s), 6.61 (1H, d), 6.38 (1H, d), 3.76 (3H, s), 3.70 (3H, t), 2.07 (2H, s), 1.94 (6H, s), 1.75–1.55 (12H, m).

EXAMPLE 44

N-(3-(3-(N-Methylamino)propyloxy)-2-methylphenyl)-tricyclo[3.3.1.1[3,7]]decane-1-acetamide, hydrochloride

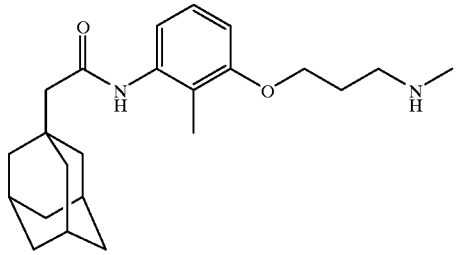

Dry dichloromethane (40 ml), triphenylphosphine (3.28 g), imidazole (1.05 g) and iodine (3.85 g) were combined in that order. A solution of tert-butyl N-(3-hydroxypropyl)-N-methylcarbamate (1.90 g, J. Org. Chem., 1988, 53(10), 2229) in dichloromethane (10 ml) was added and the resulting reaction mixture stirred at room temperature for 1 hour. An aqueous solution of sodium hydrogen sulphite (6 g in 100 ml of water) was then added and the organic layer separated. The latter was dried over anhydrous magnesium sulphate, filtered and concentrated under reduced pressure. The residue was purified by column chromatography over silica eluting with iso-hexane:ether (7:3) to give tert-butyl N-(3-iodopropyl)-N-methylcarbamate (2.54 g) which was used immediately. Caesium carbonate (0.655 g) was added to a suspension of N-(3-hydroxy-2-methylphenyl)-tricyclo [3.3.1.1$^{3,7}$]decane-1-acetamide (0.453 g, Example 26) in acetonitrile (35 ml) and the mixture heated at 100° C. for 10 minutes. After cooling to room temperature a solution of tert-butyl N-(3-iodopropyl)-N-methylcarbamate (0.600 g) in acetonitrile (5 ml) was added and the reaction heated at reflux for 90 minutes. The reaction was concentrated under reduced pressure and the residue partitioned between dichloromethane (100 ml) and water (100 ml). The organic layer was dried over anhydrous magnesium sulphate, filtered and concentrated under reduced pressure. The residue was purified by silica gel chromatography eluting with dichloromethane:ethyl acetate (9:1) to give a solid that was dissolved in methanol (10 ml). A solution of hydrogen chloride (generated by slow addition of acetyl chloride (12 ml) to methanol (15 ml) at 0° C. CARE—Very Exothermic) was then added to the latter solution and the reaction stirred at room temperature for 1 hour. The reaction was concentrated under reduced pressure to give a gum that was scratched under ether:hexane (1:1) (20 ml) to give the title compound as a pale yellow powder (0.477 g).

MS (APCI+ve) 371 (M−HCl+H)$^+$; $^1$H NMR (DMSO-d$_6$) δ 9.20 (1H, s), 8.82 (2H, bs), 7.10 (1H, t), 6.94 (1H, d), 6.78 (1H, d), 4.05 (2H, t), 3.15–3.0 (2H, m), 2.58 (3H, t), 2.15–2.0 (7H, m), 1.94 (3H, m), 1.75–1.55 (12H, m).

EXAMPLE 45

N-(5-(3-(N,N-Dimethylamino)propyloxy)-2-methylphenyl)tricyclo[3.3.1.1$^{3,7}$]decane-1-acetamide, hydrochloride

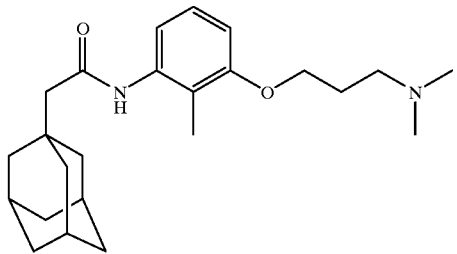

Caesium carbonate (1.31 g) was added to a suspension of N-(3-hydroxy-2-methylphenyl)-tricyclo[3.3.1.1$^{3,7}$]decane-1-acetamide (0.473 g, Example 26) in acetonitrile (35 ml) and the mixture heated at 80° C. for 5 minutes. After cooling to room temperature solid N,N-dimethyl-3-chloropropylamine (0.274 g) was added and the reaction heated at reflux overnight. The reaction was concentrated under reduced pressure and the residue partitioned between dichloromethane (100 ml) and water (100 ml). The organic layer was dried over anhydrous sodium sulphate, filtered and concentrated under reduced pressure. The residue was purified by column chromatography over silica eluting with dichloromethane:ethanol:triethylamine (95:4:1) to give a yellow gum. This was dissolved in methanol (10 ml) and treated with an excess of ethereal hydrogen chloride is (1M, 5 equivalents). The solution was concentrated under reduced pressure to give a gum that was stirred for 2 days in ether (20 ml) to give a solid which was isolated by filtration (0.588 g).

MS (APCI+ve) 385 (M−HCl+H)$^+$; $^1$H NMR (DMSO-d$_6$) δ 10.33 (1H, bs), 9.21 (1H, s), 7.10 (1H, t), 6.94 (1H, d), 6.78 (1H, d), 4.04 (2H, t), 3.3–3.1 (2H, m), 2.79 (6H, d), 2.2–2.1(2H, m), 2.08 (2H, s), 2.05 (3H, s), 1.95(3H, s), 1.75–1.55 (12H, m).

EXAMPLE 46

N-(5-Methoxy-2-methylphenyl)-tricyclo[3.3.1.1$^{3,7}$] decanyloxy-1-acetamide

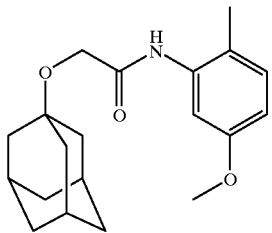

Thionyl chloride (3 ml) was added to 1-adamantyloxyacetic acid (0.38 g, CA 1966, 65, 2149a) and the reaction heated at reflux for 2 minutes. The excess thionyl chloride was removed by concentration under reduced pressure and the residue was then dissolved in dichloromethane (2.5 ml). This solution was then added over 1 minute to a solution of 5-methoxy-2-methylaniline (0.37 g) in dichloromethane (20 ml) and triethyl amine (1 ml) at room temperature. After 3 days the reaction mixture was concentrated under reduced pressure and the residue added to a column of silica. The mixture was then chromatographed eluting with dichloromethane then dichloromethane:ethyl acetate (19:1) to give a solid. This was dissolved in dichloromethane (75 ml) and the solution washed with aqueous hydrochloric acid (2M, 2×30 ml). The organic solution was dried over anhydrous magnesium sulphate, filtered and concentrated under reduced pressure. The residue was washed with ether:hexane (1:1) to give the title compound as a colourless solid (0.40 g).

Melting point: 128–130° C.; MS (APCI+ve) 330 (M+H)$^+$; $^1$H NMR (DMSO-$d_6$) δ 8.81 (1H, s), 7.46 (1H, d), 7.12 (1H, d), 6.65 (1H, dd), 4.04 (2H, s), 3.71 (3H, s), 2.15–2.12 (6H, m), 1.78 (6H, d), 1.7–1.5 (6H, m).

EXAMPLE 47

N-(5-Methoxy-2-methylphenyl)-(3-bromo-tricyclo [3.3.1.1$^{3,7}$]decane-1-acetamide

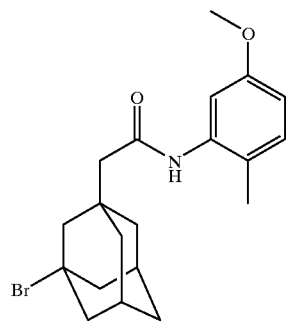

To a solution of 3-bromoadamantane acetic acid (CN 17768-34-2) (0.123 g) in dichloromethane (5 ml) was added oxalyl chloride (0.5 ml) and resulting reaction mixture heated to reflux temperature for 2 hr before concentration at reduced pressure. Residue was dissolved in dichloromethane (5 ml) and a mixture of 5-methoxy-2-methylaniline (0.062

EXAMPLE 48

N-(5-Methoxy-2-methylphenyl)-(2-oxa-tricyclo [3.3.1.1$^{3,7}$]decane)-1-acetamide

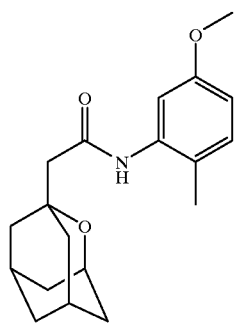

a) Ethyl (2-oxa-tricyclo[3.3.1.1$^{3,7}$]decane)-1-acetate

Sodium borohydride (0.093 g) was added to a solution of ethyl 7-oxobicyclo[3.3.1]non-3-ylideneacetate (0.113 g, Chem.Pharm.Bull., 1979, 27, 824) in ethanol (2 ml) and the reaction left to stir at room temperature for 3 days. Reaction was diluted with dichloromethane (60 ml) and washed with a saturated solution of aqueous ammonium chloride (20 ml). The organic phase was dried over anhydrous magnesium sulphate, filtered and concentrated under reduced pressure. The residue was purified by column chromatography over silica eluting with dichloromethane and then dichloromethane:ether (9:1) to give the sub-title compound as an oil (0.078 g).

$^1$H NMR (CDCl$_3$) δ 4.15 (2H, q), 4.09 (1H, bs), 2.37 (2H, s), 2.16 (2H, bs), 2.2–1.5 (10H, m), 1.27 (3H, t).

b) N-(5-Methoxy-2-methylphenyl)-(2-oxa-tricyclo [3.3.1.1$^{3,7}$]decane)-1-acetamide Aqueous sodium hydroxide (10%, 2 ml) was added to a solution of ethyl (2-oxa-tricyclo[3.3.1.1$^{3,7}$]decane)-1-acetate (66 mg) in ethanol (2 ml). After stirring at room temperature for 1 hour the solvent was removed under reduced pressure. The residue was partitioned between aqueous hydrochloric acid (2M, 6 ml) and dichloromethane (2×20 ml). The organic extracts were dried over anhydrous magnesium sulphate, filtered and concentrated under reduced pressure to give (2-oxa-tricyclo[3.3.1.1$^{3,7}$]decane)-1-acetic acid. Thionyl chloride (3 ml) was added to the acid and the reaction heated at reflux for 2 minutes. The excess thionyl chloride was removed by concentration under reduced pressure and the residue was then dissolved in dichloromethane (5 ml). This solution was then added over 1 minute to a solution of 5-methoxy-2-methylaniline (69 mg) in dichloromethane (5 ml) and triethylamine (1 ml) at room temperature for 20 minutes. The reaction mixture was diluted with dichloromethane to 60 ml and then washed with aqueous hydrochloric acid (2M, 30 ml). The organic phase was dried over anhydrous magnesium sulphate, filtered and concentrated under reduced pressure. The residue was purified by column chromatography over silica eluting with dichloromethane then dichloromethane: ether (19:1) to give, after trituration with iso-hexane, a colourless solid (0.05 g).

Melting point: 108–109.5° C.; MS (APCI+ve) 316 (M+H)$^+$; $^1$H NMR (DMSO-d$_6$) δ 9.12 (1H, s), 7.39 (1H, d), 7.08 (1H, d), 6.61 (1H, dd), 4.09 (1H, bs), 3.69 3H, s), 2.37 (2H, s), 2.15–2.05 (2H, m), 2.13 (3H, s), 1.69–1.55 (10H, m).

EXAMPLE 49

N-(5-Methoxy2-methylphenyl)-2-(tricyclo [3.3.1.1$^{3,7}$]decan-1-amino)acetamide

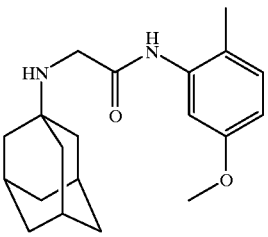

a) N-(5-Methoxy-2-methylphenyl)-2-chloroacetamide

To a solution of 5-methoxy-2-methylaniline (7.62 g) and triethylamine (15.5 ml) in dichloromethane (150 ml) at 0–5° C. was added chloroacetyl chloride (5.0 ml) dropwise and the ice bath removed. The resulting reaction mixture was stirred for 45 min before being poured into dil HCl and extracted with dichloromethane. Organic extracts were combined, washed with water, dried (Na$_2$SO$_4$) and concentrated to give a brown solid that was triturated with diethyl ether to leave the sub-title compound as a beige solid (5.7 g).

Melting point: 89–91° C.; $^1$H NMR (DMSO-d$_6$) δ 9.58 (1H, s), 7.12 (1H, d), 7.05 (1H, d), 6.71 (1H, dd), 4.30 (2H, s), 3.71 (3H, s), 2.13 (3H, s).

b) N-(5-Methoxy-2-methylphenyl)-2-(tricyclo[3.3.1.1$^{3,7}$] decan-1-amino)acetamide A solution of chloroamide from step a) (0.092 g), adamantanamine (0.13 g), diisopropylethylamine (0.17 ml) and tetrahydrofuran (1.5 ml) was heated in a sealed Wheaton vial to 100° C. for 18 hr. Reaction mixture cooled to room temperature and poured into water and extracted with diethyl ether. Organic extracts combined, washed with brine, dried (Na$_2$SO$_4$) and concentrated and residue purified by column chromatography over silica eluting 0–2% methanol in dichloromethane to give the title compound as a white solid (0.034 g).

Melting point: 158° C.; MS (APCI+ve) 329 (M+H)$^+$; $^1$H NMR (DMSO-d$_6$) δ 9.92 (1H, s), 7.76 (1H, d), 7.10 (1H, d), 6.57 (1H, dd), 3.69 (3H, s), 3.22 (2H, s), 2.27 (1H, br s), 2.18 (3H, s), 2.01 (3H, s), 1.58 (12H, s).

EXAMPLE 50

N-(3,5-Dimethoxyphenyl)-tricyclo[3.3.1.1³,⁷]decane-1-acetamide

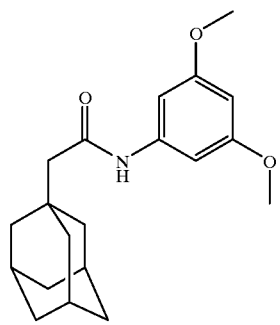

Prepared according to the method of Example 39 from 1-adamantaneacetic acid (3.0 g) and 3,5-dimethoxyaniline (3.0 g) to give the title compound as a white solid (4.2 g).

Melting point: 144–146° C.; MS (APCI+ve) 330 (M+H)$^+$; $^1$H NMR (DMSO-d$_6$) δ 9.69 (1H, S), 6.86 (2H, d), 6.18 (1H, t), 3.70 (6H, s), 2.02 (2H, s), 1.93 (3H, s), 1.68–1.57 (12H, m).

EXAMPLE 51

N-(3,5-Dihydroxyphenyl)-tricyclo[3.3.1.1³,⁷]decane-1-acetaniide

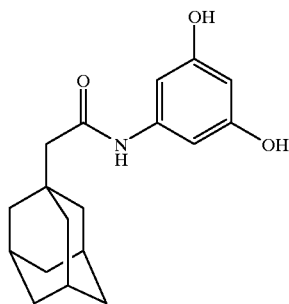

To a solution of N-(3,5-dimethoxyphenyl)-tricyclo[3.3.1.1³,⁷]decane-1-acetamide (2.22 g) in dichloromethane (200 ml) at −78° C. was added boron tribromide (60 ml of a 1M solution in dichloromethane). Cooling bath was removed and reaction stirred at room temperature for 3 days. Reaction was quenched by addition of ice (230 g). After stirring vigorously for 30 min ethyl acetate (700 ml) added and the organic layer separated, dried (MgSO$_4$) and concentrated. The residue was purified by column chromatography over silica eluting 5% ethanol in dichloromethane to give the leave a white solid (1.95 g). A portion of this was recrystallised from hot ethyl acetate to leave the title compound as an off-white solid.

Melting point: 239–242° C.; MS (APCI+ve) 302 (M+H)$^+$; $^1$H NMR (DMSO-d$_6$) δ 9.42 (1H, s), 9.09 (2H, s), 6.55 (2H, d), 5.87 (1H, t), 1.99 (2H, s), 1.92 (3H, s), 1.69–1.56 (12H, m).

EXAMPLE 52

N-(3,5-Dimethoxyphenyl)-tricyclo[3.3.1.1³,⁷]decanyloxy-1-acetamide

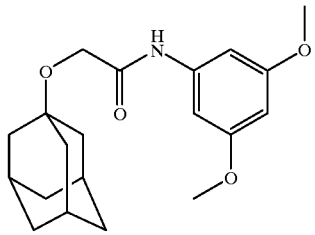

Prepared according to the method of Example 46 using 1-adamantyloxyacetic acid (2.0 g) and 3,5-dimethoxyaniline (1.75 g) to leave the title compound as an oil (2.5 g).

MS (APCI+ve) 346 (M+H)$^+$; $^1$H NMR (DMSO-d$_6$) δ 9.23 (1H, s), 6.94 (2H, s), 6.23 (1H, s), 3.98 (2H, s), 3.71 (6H, s), 2.12 (3H, s), 1.76(6H, d), 1.59 (6H, m).

EXAMPLE 53

N-(3,5-Bis-(3-aminopropyloxy)phenyl)-tricyclo[3.3.1.1³,⁷]decane-1-acetamide

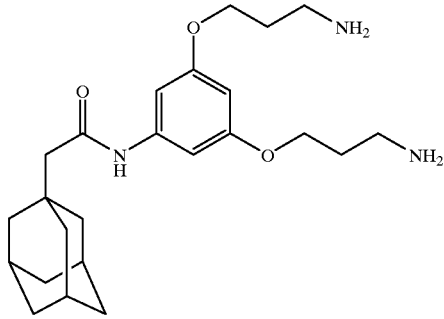

Prepared according to the method of Example 2 using N-(3,5-dihydroxyphenyl)-tricyclo[3.3.1.1³,⁷]decane-1-acetamide from Example 51 (0.60 g), tert-butyl N-(3-hydroxypropyl)carbamate (1.43 g), tributylphosphite (2.0 ml) and 1,1'(azodicarbonyl)dipiperidine (2.05 g) to leave the title compound as a fawn solid (0.12 g).

MS (APCI+ve) 416 (M+H)$^+$; $^1$H NMR (DMSO-d$_6$) δ 9.81 (1H, s), 8.00 (6H, br s), 6.91 (2H, d), 6.22 (1H, t), 4.00 (4H, t), 2.93 (4H, t), 2.04–1.98 (9H, m), 1.69–1.56 (12H, m).

EXAMPLE 54

N-(2,4,5-Trimethylphenyl)-tricyclo[3.3.1.1³,⁷]decanyloxy-1-acetamide

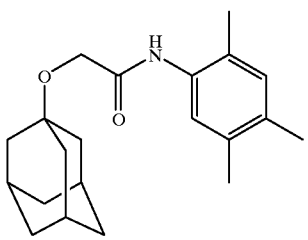

The title compound was prepared as in Example 46 from 2,4,5-trimethylaniline (0.30 g) and 1-adamantyloxyacetic acid (0.38 g, CA 1966, 65, 2149a) as a colourless solid (0.41 g).

Melting point: 138–140° C.; MS (APCI+ve) 328 (M+H)⁺; ¹H NMR (DMSO-$d_6$) δ 8.76 (1H, s), 7.42 (1H, s), 6.98 (1H, s), 4.00 (2H, s), 2.2–2.1 (12H, m), 1.8–1.75 (6H, m), 1.65–1.55 (6H, m).

EXAMPLE 55

N-(5-Hydroxy-2-methylphenyl)-tricyclo[3.3.1.1³,⁷]decanyloxy-1-acietamide

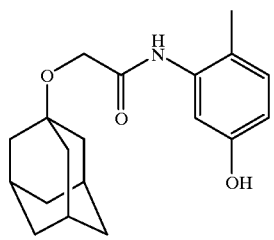

Thionyl chloride (5 ml) was added to 1-adamantyloxyacetic acid (2.00 g, CA 1966, 65, 2149a) and the reaction heated at reflux for 5 minutes. The excess thionyl chloride was removed by concentration under reduced pressure and the residue was then dissolved in dichloromethane (10 ml). This solution was then added over 5 minutes to a solution of 2-methyl-5-hydroxyaniline hydrochloride (1.00 g J.Chem.Soc. Perkin Trans. 2, 1972, 539) in dichloromethane (20 ml) and triethylamine (10 ml) at 0° C. The solution was then allowed to warm to room temperature and, after 30 minutes stirring, was concentrated under reduced pressure. The residue was dissolved in methanol (20 ml) and tetrahydrofuran (10 ml) and was treated with a solution of sodium methoxide in methanol (25 wt. %, 10 ml). After 15 minutes stirring the reaction was treated with formic acid (4 ml) and then concentrated under reduced pressure. The residue was partitioned between aqueous hydrochloric acid (2M, 90 ml), ethyl acetate (90 ml) and tetrahydrofuran (50 ml). The organic phase was separated, washed with saturated aqueous sodium chloride (50 ml), dried over anhydrous magnesium sulphate, filtered and concentrated under reduced pressure to give a solid (2.62 g). This was purified by column chromatography over silica eluting with dichloromethane:ethyl acetate (4:1) to give a colourless solid (1.39 g).

Melting point: 258° C. (dec.); MS (APCI+ve) 316 (M+H)⁺; ¹H NMR (DMSO-$d_6$) δ 9.22 (1H, s), 8.71 (1H, s), 7.37 (1H, d), 6.98 (1H, d), 6.45 (1H, dd), 4.02 (2H, s), 2.13(3H, bs), 2.10 (3H, s), 2.15–2.12 (6H, m), 1.78 (6H, d), 1.7–1.5 (6H, m).

EXAMPLE 56

N-(5-(2-(N-Methylamiino)ethyloxy)-2-methylphenyl)-tricyclo[3.3.1.1³,⁷]decane-1-acetamide, hydrochloride

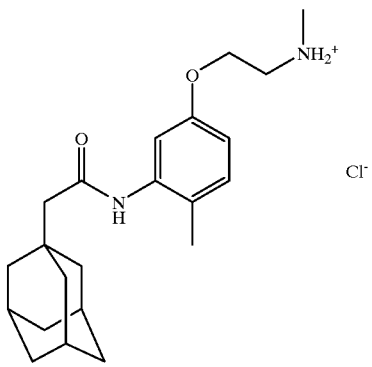

Tert-butyl-N-(2-hydroxyethyl)-N-methylcarbamate (1.05 g, Synth. Commun., 1993, 23(17), 2443), N-(5-hydroxy-2-methylphenyl)-tricyclo[3.3.1.1³,⁷]decane-1-acetamide (100 g, Example 12), tetrahydrofuran (40 ml) and tributylphosphine (1.35 ml) were combined, cooled in ice/water, before addition of 1,1'-(azodicarbonyl)dipiperidine (1.39 g) and reaction stirred for 10 minutes. After stirring at room temperature for 90 minutes further tert-butyl N-(2-hydroxyethyl)-N-methylcarbamate (1.04 g) and tributylphosphine (1.35 ml) were added and the solution recooled in ice/water before addition of 1,1'-(azodicarbonyl) dipiperidine (1.39 g) and stir in ice/water for 10 minutes then at room temperature overnight. The reaction mixture was diluted with iso-hexane (50 ml) and filtered. The residue was washed with ether (100 ml) and the combined organics concentrated under reduced pressure. The residue was purified by column chromatography over silica eluting with iso-hexane:ethyl acetate (7:3) and further purified by column chromatography over silica eluting with dichloromethane:ethyl acetate (9:1) to give the coupled product (0.57 g) which was dissolved in methanol (10 ml). A solution of hydrogen to chloride (generated by slow addition of acetyl chloride (10 ml) to methanol (15 ml) at 0° C. CARE—Very Exothermic) was then added to the latter solution and the reaction stirred at room temperature for 2 hours. The reaction was then concentrated under reduced pressure and then triturated with ether (100 ml) give the title compound as colourless solid (0.35 g).

Melting point: 193–195° C.; MS (APCI+ve) 357 (M+H)⁺ as free base. ¹H NMR (DMSO-$d_6$) δ 9.06 (1H, s), 8.91 (2H, bs), 7.19 (1H, 6), 7.12 (1H, d), 6.70 (1H, dd), 4.17 (2H, t), 3.4–3.25 (2H, m), 2.61 (3H, s), 2.15 (3H, s), 2.11 (2H, s), 1.95 (3H, s), 1.75–1.55 (12H, m).

EXAMPLE 57

N-(5-(2-(N-Methylamino)ethyloxy)-2-methylphenyl)-tricyclo[3.3.1.1$^{3,7}$]decanyloxy-1-acetamide

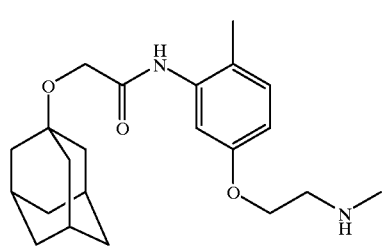

a) N-(5-Hydroxy-2-methylphenyl)-tricyclo[3.3.1.1$^{3,7}$]decanyloxy-1-acetamide

Thionyl chloride (5 ml) was added to 1-adamantyloxyacetic acid (2.00 g, CA 1966, 65, 2149a) and the reaction heated at reflux for 5 minutes. The excess thionyl chloride was removed by concentration under reduced pressure and the residue was dissolved in dichloromethane (10 ml). This solution was added over 5 minutes to a solution of 5-hydroxy-2-methylaniline, hydrochloride (1.00 g J.Chem.Soc. Perkin Trans. 2, 1972, 539) in dichloromethane (20 ml) and triethylamine (10 ml) at 0° C. The solution was allowed to warm to room temperature and, after 30 minutes stirring, was concentrated under reduced pressure. The residue was dissolved in methanol (20 ml) and tetrahydrofuran (10 ml) and was treated with a solution of sodium methoxide in methanol (25 wt. %, 10 ml). After 15 minutes stirring the reaction was treated with formic acid (4 ml) and concentrated under reduced pressure. The residue was partitioned between aqueous hydrochloric acid (2M, 90 ml), ethyl acetate (90 ml) and tetrahydrofuran (50 ml). The organic phase was separated, washed with saturated aqueous sodium chloride (50 ml), dried over anhydrous magnesium sulphate, filtered and concentrated under reduced pressure. The residue was purified by column chromatography over silica eluting with dichloromethane:ethyl acetate (4:1) to give the sub-title compound as a colourless solid (1.39 g).

Melting point: 258° C. (dec.); MS (APCI+ve) 316 (M+H)$^+$; $^1$H NMR (DMSO-$d_6$) δ 9.22 (1H, s), 8.71 (1H, s), 7.37 (1H, d), 6.98 (1H, d), 6.45 (1H, dd), 4.02 (2H, s), 2.13(3H, bs), 2.10 (3H, s), 2.15–2.12 (6H, m), 1.78 (6H, d), 1.7–1.5 (6H, m).

b) N-(5-(2-(N-Methylamino)ethyloxy)-2-methylphenyl)-tricyclo[3.3.1.1$^{3,7}$]decanyloxy-1-acetamide Prepared using the method described in Example 2 using tert-butyl N-(2-hydroxyethyl)-N-methylcarbamate (1.05 g, Synth. Commun., 1993, 23(17), 2443) and N-(5-hydroxy-2-methylphenyl)-tricyclo[3.3.1.1$^{3,7}$]decanyloxy-1-acetamide (1.00 g, part a) to give the title compound as a colourless solid (0.54 g).

Melting point: 155–158° C. (dec.); MS (APCI+ve) 373 (M−HCl+H)$^+$; $^1$H NMR (DMSO-$d_6$) δ 9.07 (2H, bs), 8.84 (1H, s), 7.57 (1H, d), 7.16 (1H, d), 6.71 (1H, dd), 4.20(2H, t), 4.05 (2H, s), 3.30 (2H, t), 2.60 (3H, t), 2.17 (3H, s), 2.13 (3H, s), 1.78 (6H, d), 1.65–1.55 (6H, m).

EXAMPLE 58

N-(5-(3-(N-Methylamino)propyloxy)-2-methylphenyl)-tricyclo[3.3.1.1$^{3,7}$]decanyloxy-1-acetamide

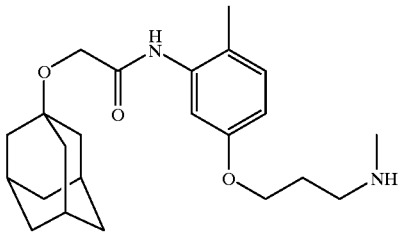

Prepared using the method described in Example 56 from tert-butyl N-(3-hydroxypropyl)-N-methylcarbamate (1.01 g, J. Org. Chem., 1988, 53(10), 2229) and N-(5-hydroxy-2-methylphenyl)-tricyclo[3.3.1.1$^{3,7}$]decanyloxy-1-acetamide (1.00 g, Example 55) to give the title compound as a colourless solid (0.50 g).

Melting point: 151–154° C. (dec.); MS (APCI+ve) 387 (M−HCl+H)$^+$; $^1$H NMR (DMSO-$d_6$) δ 8.91 (2H, bs), 8.82 (1H, s), 7.49 (1H, d), 7.13 (1H, d), 6.67 (1H, dd), 4.04 (2H, s), 4.01(2H, t), 3.03 (2H, quintet), 2.55 (3H, t), 2.15(3H, s), 2.13 (3H, s), 2.06 (2H, quintet), 1.78 (6H, d), 1.65–1.55 (6H, m).

EXAMPLE 59

N-(3,5-Dihydroxy-2-methylphenyl)-tricyclo[3.3.1.1$^{3,7}$]decane-acetamide

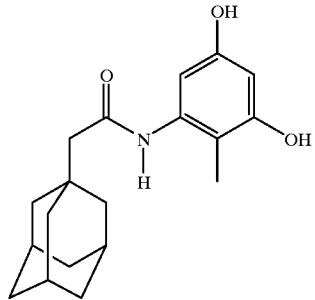

A solution of dimethoxy ether from Example 43 (2.0 g) in 50% hycdrobromic acid in acetic acid was heated at 100 degrees for 12 hours. The solution was concentrated under vacuum, the residue taken in water and extracted with ethyl acetate. The organic layers were dried over magnesium sulfate, filtered, concentrated under vacuum. The crude material was purified over silica eluting with dichloromethane' ethyl acetateto afford the title compound as a white solid.

Melting point: 270° C. (dec.); MS (APCI+ve) 316 (M+H)$^+$; $^1$H NMR (CDCl$_3$) δ 9.09(1H, s); 8.91(1H, s); 8.86(1H, bs); 6.35(1H, d); 6.11(4H, d); 2.04(2H, s); 1.94 (3H, bs); 1.87(3H, s); 1.80–1.50(12H, m).

EXAMPLE 60

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of $P2X_7$ receptor activation and therefore to quantify the effect of a compound on the $P2X_7$ receptor.

In this manner, each of the title compounds of Examples 1 to 59 were tested for antagonist activity at the $P2X_7$ receptor. Thus, the test was performed in 96-well flat bottomed microtitre plates, the wells being filled with 250 μl of test solution comprising 200 μl of a suspension of THP-1 cells ($2.5 \times 10^6$ cells/ml) containing $10^{-4}$ M ethidium bromide, 25 μl of high potassium buffer solution containing $10^{-5}$ M bbATP, and 25 μl of high potassium buffer solution containing $3 \times 10^{-5}$ M test compound. The plate was covered with a plastics sheet and incubated at 37° C. for one hour. The plate was then read in a Perkin-Elmer fluorescent plate reader, excitation 520 nm, emission 595 nm, slit widths:Ex 15 nm, Em 20 nm. For the purposes of comparison, bbATP (a $P2X_7$ receptor agonist) and pyridoxal 5-phosphate (a $P2X_7$ receptor antagonist) were used separately in the test as controls. From the readings obtained, a $pIC_{50}$ figure was calculated for each test compound, this figure being the negative logarithm of the concentration of test compound necessary to reduce the bbATP agonist activity by 50%. Each of the compounds of Examples 1 to 59 demonstrated antagonist activity, having a $pIC_{50}$ figure >4.50.

What is claimed is:

1. A compound of general formula

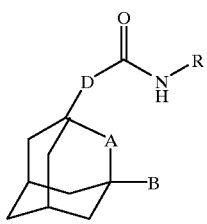

(I)

wherein A represents a $CH_2$ group;

B represents a hydrogen or halogen atom;

D represents a group $CH_2$, $OCH_2$, $NHCH_2$ or $CH_2CH_2$;

R represents a phenyl group, which may be optionally substituted by one or more substituents independently selected from a halogen atom or a cyano, carboxyl, hydroxyl, nitro, halo-$C_1$-$C_6$-alkyl, —N($R^1$)—C(=O)—$R^2$, —C(O)$NR^3R^4$, —$NR^5R^6$, $C_3$-$C_8$-cycloalkyl, 3- to 8-membered heterocyclyl, $C_3$-$C_8$-cycloalkyloxy, $C_1$-$C_6$-alkylcarbonyl, phenoxy, benzyl, $C_1$-$C_6$-alkylthio, phenylthio, $C_1$-$C_6$-alkoxycarbonyl, $C_1$-$C_6$-alkylsulphinyl or $C_1$-$C_6$-alkylsulphonyl group, or a $C_1$-$C_6$-alkyl or $C_1$-$C_6$-alkoxy group optionally substituted by one or more substituents independently selected from a halogen atom or an amino, carboxyl, hydroxyl, $C_1$-$C_6$-alkoxy, (di)$C_1$-$C_6$-alkylamino, $C_1$-$C_6$-alkoxycarbonyl, imidazolyl, morpholinyl, piperldinyl or pyrrolidinyl group;

$R^1$ represents a hydrogen atom or a $C_1$-$C_6$-alkyl or $C_3$-$C_8$-cycloalkyl group;

$R^2$ represents a $C_1$-$C_6$-alkyl or $C_3$-$C_8$-cycloalkyl group; and $R^3$, $R^4$, $R^5$ and $R^6$ each independently represent a hydrogen atom or a $C_1$-$C_6$-alkyl or $C_3$-$C_8$-cycloalkyl group;

with the provisos that (i) when A is $CH_2$, B is H and D is $CH_2$, then R does not represent a phenyl, ortho-carboxyphenyl, ortho-nitrophenyl, ortho-aminophenyl, ortho-(dimethylaminoethyl)phenyl, methylphenyl or para-phenoxyphenyl group, and (ii) when A is $CH_2$, B is Br and D is $CH_2$, then R does not represent an orthocarboxyphenyl group, and (iii) when A is $CH_2$, B is H and D is $CH_2CH_2$, then R does not represent a phenyl group, and (iv) when A is $CH_2$ D is $CH_2$ or $CH_2CH_2$ and R represents a substituted phenyl group, the substituent or substituents present do not comprise, in an ortho position, a $C_1$-$C_6$-alkoxy group substituted by an amino, (di)$C_1$-$C_6$-alkylamino, imidazolyl, morpholinyl, piperidinyl or pyrrolidinyl group;

or a pharmaceutically acceptable salt or solvate thereof.

2. A compound according to claim 1, wherein B represents a hydrogen atom.

3. A compound according to claim 1, wherein D represents a group $CH_2$, $OCH_2$ or $NHCH_2$.

4. A compound according to claim 1, wherein R represents a phenyl which may be optionally substituted by one, two or three substituents independently selected from a halogen atom or a hydroxyl, nitro or $C_1$-$C_4$-alkoxycarbonyl group, or a $C_1$-$C_4$-alkyl or $C_1$-$C_4$-alkoxy group optionally substituted by one or two substituents independently selected from of a halogen atom or an amino, carboxyl, hydroxyl, $C_1$-$C_4$-alkoxy, (di)$C_1$-$C_4$-alkylamino, $C_1$-$C_4$-alkoxycarbonyl, imidazolyl, morpholinyl, piperidinyl or pyrrolidinyl group.

5. A compound of formula (I) as defined in claim 1, or a pharmaceutically acceptable salt or solvate thereof, being:

N-(3-(3-(Aminopropyloxy)-2-methylphenyl)-tricyclo[3.3.1.1$^{3,7}$]decane-1-acetamide, hydrochloride, N-(2-Chlorophenyl)-tricyclo[3.3.1.1$^{3,7}$]decane-1-acetamide, N-(2,4,5-Trimethylphenyl)-tricyclo[3.3.1.1$^{3,7}$]decane-1-acetamide, N-(5-Methoxy-2-methylphenyl)-tricyclo[3.3.1.1$^{3,7}$]decane-1-acetamide, N-(2,3-Dimethylphenyl)-tricyclo[3.3.1.1$^{3,7}$]decane-1-acetamide, N-[5-(3-N,N-Dimethylaminopropoxy)-2-methylphenyl]-tricyclo[3.3.1.1$^{3,7}$]decane-1-acetamide, hydrochloride, N-(5-Hydroxy-2-methylphenyl)-tricyclo[3.3.1.1$^{3,7}$]decane-1-acetamide, 4-Methyl-3-[[1-oxo-2-(tricyclo[3.3.1.1$^{3,7}$]dec-1-yl)ethyl]amino]phenoxy-acetic acid, hydrochloride salt, N-(4-Methoxy-2-methylphenyl)-tricyclo[3.3.1.1$^{3,7}$]decane-1-acetamide, N-(2-Chloro-5-methoxyphenyl)-tricyclo[3.3.1.1$^{3,7}$]decane-1-acetamide, N-(4-Hydroxy-2-methylphenyl)-tricyclo[3.3.1.1$^{3,7}$]decane-1-acetamide, N-(3-Hydroxymethyl-2-methylphenyl)-tricyclo[3.3.1.1$^{3,7}$]decane-1-acetamide, N-(5-Methoxy-2-methyl-3-nitrophenyl)-tricyclo[3.3.1.1$^{3,7}$]decane-1-acetamide, N-(5-Hydroxymethyl-2-methylphenyl)-tricyclo[3.3.1.1$^{3,7}$]decane-1-acetamide, N-(3-Hydroxy-2-methylphenyl)-tricyclo[3.3.1.1$^{3,7}$]decane-1-acetamide, N-(2-Methyl-5-(1-pyrrolidinemethyl)phenyl)-tricyclo[3.3.1.1$^{3,7}$]decane-1-acetamide, hydrochloride, N-(2-Chloro-5-hydroxyphenyl)-tricyclo[3.3.1.1$^{3,7}$]decane-1-acetamide,
N-(2-Chloro-4-hydroxyphenyl)-tricyclo[3.3.1.1$^{3,7}$]decane-1-acetamide,
N-(2-Methyl-3-(2-(1-pyrrolidino)ethyloxy)phenyl)-tricyclo[3.3.1.1$^{3,7}$]decane-1-acetamide, hydrochloride,
N-(5-Methoxymethyl-2-methylphenyl)-tricyclo[3.3.1.1$^{3,7}$]decane-1-acetamide,
N-(2-Methyl-3-(2-(1-morpholino)ethyloxy)phenyl)-tricyclo[3.3.1.1$^{3,7}$]diecane-1-acetamide, hydrochloride,
N-(2-Methyl-3-(2-1-piperidino)ethyloxy)phenyl)-tricyclo[3.3.1.1$^{3,7}$]decane-1-acetamide, hydrochloride,
N-(2-Methyl-5-(1-morpholinomethyl)phenyl)-tricyclo[3.3.1.1$^{3,7}$]decane-1-acetamide, hydrochloride,
N-(3-Methoxy-2-methylphenyl)-tricyclo[3.3.1.1$^{3,7}$]decane-1-acetamide,
N-(2-Methyl-3-(2-(1-imidazolo)ethyloxy)phenyl)-tricyclo[3.3.1.1$^{3,7}$]decane-1-acetamide,
N-(2,4,6-Trimethylphenyl)-tricyclo[3.3.1.1$^{3,7}$]decane-1-acetamide,
N-(5-(3-Aminopropyloxy)-2-methylphenyl)-tricyclo[3.3.1.1$^{3,7}$]decane-1-acetamide, hydrochloride,
N-(5-(3-(N-Methylamino)propyloxy)-2-methylphenyl)-tricyclo[3.3.1.1$^{3,7}$]decane-1-acetamide, hydrochloride,
N-(3,5-Dimethoxy-2-methylphenyl)-tricyclo[3.3.1.1$^{3,7}$]decane-1-acetamide,
N-(3-(3-(N-Methylamino)propyloxy)-2-methylphenyl)-tricyclo[3.3.1 1$^{3,7}$]decane-1-acetamide, hydrochloride,
N-(5-(3-(N,N-Dimethylamino)propyloxy)-2-methylphenyl)-tricyclo[3.3.1.1$^{3,7}$]decane-1-acetamide, hydrochloride,
N-(5-Methoxy-2-methylphenyl)-tricyclo[3.3.1.1$^{3,7}$]decanyloxy-1-acetamide,
N-(5-Methoxy-2-methylphenyl)-(3-bromo-tricyclo[3.3.1.1$^{3,7}$]decane)-1-acetamide,
N-(5-Methoxy-2-methylphenyl)-(2-oxa-tricyclo[3.3.1.1$^{3,7}$]decane)-1-acetamide,
N-(5-Methoxy-2-methylphenyl)-2-(tricyclo[3.3.1.1$^{3,7}$]decan-1-amino)acetamide,
N-(3,5-Dimethoxyphenyl)-tricyclo[3.3.1.1$^{3,7}$]decan-1-acetamide,
N-(3,5-Dihydroxyphenyl)-tricyclo[3.3.1.1$^{3,7}$]decan-1-acetamide,
N-(3,5-Dimethoxyphenyl)-tricyclo[3.3.1.1$^{3,7}$]decanyloxy-1-acetamide,
N-(3,5-Bis-(3-aminopropyloxy)phenyl)-tricyclo[3.3.1.1$^{3,7}$]decane-1-acetamide,
N-(2,4,5-Trimethylphenyl)-tricyclo[3.3.1.1$^{3,7}$]decanyloxy-1-acetamide,
N-(5-Hydroxy-2-methylphenyl)-tricyclo[3.3.1.1$^{3,7}$]decanyloxy-1-acetamide,
N-(5-(2-(N-Methylamino)ethyloxy)-2-methylphenyl)-tricyclo[3.3.1.1$^{3,7}$]decane-1-acetamide, hydrochloride,
N-(5-(2-(N-Methylamino)ethyloxy)-2-methylphenyl)-tricyclo[3.3.1.1$^{3,7}$]decanyloxy-1-acetamide,
N-(5-(3-(N-Methylamino)propyloxy)-2-methylphenyl)-tricyclo[3.3.1.1$^{3,7}$]decanyloxy-1-acetamide, or
N-(3,5-Dihydroxy-2-methylphenyl)-tricyclo[3.3.1.1$^{3,7}$]decane-acetamide.

6. A process for the preparation of a compound of formula (I) as defined in claim 1 which comprises reacting a compound of general formula

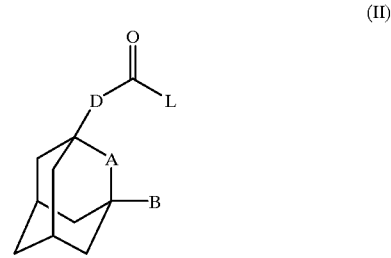

(II)

wherein L represents a leaving group and A, B and D are as defined in formula (I), with a compound of general formula (III), R-NH$_2$ wherein R is as defined in formula (I); and optionally forming a pharmaceutically acceptable salt or solvate thereof.

7. A pharmaceutical composition comprising a compound of formula (I), or a pharmaceutically acceptable salt or solvate thereof, as claimed in claims 1 in association with a pharmaceutically acceptable adjuvant, diluent or carrier.

8. A process for the preparation of a pharmaceutical composition as claimed in claim 7 which comprises mixing a compound of formula (I), or a pharmaceutically acceptable salt or solvate thereof, as defined in any one of claims 1 to 6 with a pharmaceutically acceptable adjuvant, diluent or carrier.

9. A compound of formula (I), or a pharmaceutically acceptable salt or solvate thereof, as claimed in any one of claim 1 for use in therapy.

10. A compound of formula (I), or a pharmaceutically acceptable salt or solvate thereof, as claimed in claim 1 for use in the treatment of rheumatoid arthritis.

11. A method of effecting immunosuppression which comprises administering to a patient a therapeutically effective amount of a compound of formula (I), or a pharmaceutically acceptable salt or solvate thereof, as claimed in claim 1.

* * * * *